US012569591B2

(12) United States Patent     (10) Patent No.:   US 12,569,591 B2

Amiri et al.     (45) Date of Patent:    Mar. 10, 2026

(54) MXENE-AROMATIC THERMOSETTING COPOLYESTER NANOCOMPOSITE AS AN EXTREMELY WEAR-RESISTANT BIOCOMPATIBLE IMPLANT MATERIAL FOR OSTEOARTHRITIS APPLICATIONS

(71) Applicants: The Texas A&M University System, College Station, TX (US); ATSP Innovations, Houston, TX (US)

(72) Inventors: Ahmad Amiri, College Station, TX (US); Kian Bashandeh, College Station, TX (US); Andreas A. Polycarpou, College Station, TX (US); Mohammed Saifur Rahman, Houston, TX (US)

(73) Assignees: The Texas A&M University System, College Station, TX (US); ATSP Innovations, Houston, TX (US)

( * ) Notice: Subject to any disclaimer, the term of this patent is extended or adjusted under 35 U.S.C. 154(b) by 559 days.

(21) Appl. No.: 18/191,918

(22) Filed: Mar. 29, 2023

(65) Prior Publication Data

US 2023/0310705 A1     Oct. 5, 2023

Related U.S. Application Data

(60) Provisional application No. 63/362,154, filed on Mar. 30, 2022.

(51) Int. Cl.
*A61L 27/30*     (2006.01)
*A61L 27/40*     (2006.01)
*C08J 3/12*     (2006.01)
*C08J 3/24*     (2006.01)

(52) U.S. Cl.
CPC ............... *A61L 27/30* (2013.01); *A61L 27/40* (2013.01); *C08J 3/12* (2013.01); *C08J 3/24* (2013.01); *C08J 2367/00* (2013.01)

(58) Field of Classification Search
CPC ... A61L 27/30; A61L 27/40; C08J 3/12; C08J 3/24; C08J 2367/00
See application file for complete search history.

(56) References Cited

PUBLICATIONS

Bakir, Mete, et al. "Aromatic thermosetting copolyester bionanocomposites as reconfigurable bone substitute materials: Interfacial interactions between reinforcement particles and polymer network." Scientific reports 8.1 (2018): 14869. (Year: 2018).*

* cited by examiner

*Primary Examiner* — Jerrah Edwards
*Assistant Examiner* — Jose H. Trevino, III
(74) *Attorney, Agent, or Firm* — Thomas | Horstemeyer, LLP

(57) ABSTRACT

Disclosed herein are MXene-aromatic thermosetting copolyester nanocomposites. In one aspect, the nanocomposites can be used to fabricate and/or coat artificial bone implants. In another aspect, the nanocomposites are biocompatible and/or nontoxic. Implants and coatings formed from the nanocomposites possess excellent compressive strength, hardness, and wear resistance in synovial fluid when compared to current implant coatings and materials.

20 Claims, 14 Drawing Sheets
(7 of 14 Drawing Sheet(s) Filed in Color)

LIVE/DEAD Assay Day 1 (Rat's MSC)

MXENE-AROMATIC THERMOSETTING COPOLYESTER NANOCOMPOSITE AS AN EXTREMELY WEAR-RESISTANT BIOCOMPATIBLE IMPLANT MATERIAL FOR OSTEOARTHRITIS APPLICATIONS

CROSS-REFERENCE TO RELATED APPLICATIONS

This application claims the benefit of U.S. Provisional Application No. 63/362,154, filed on Mar. 30, 2022, which is incorporated herein by reference in its entirety.

BACKGROUND

Over 30 million people in the United States are suffering from activity-limiting pain and joint damage of osteoarthritis. Specifically, knee osteoarthritis is reported to be observed in almost half of the older patients with this disease. Furthermore, the probability of hip and knee replacement is remarkably increasing and estimated to rise to around 100,000 in 2030, with hospitalization and healthcare cost higher than 2 billion US dollars. In fact, aseptic loosening accompanied by periprosthetic osteolysis is a major reason for the replacement necessity of knee implants after 5 years, which is mostly caused by their weak tribological properties. There has been a growing interest in the design and manufacturing of wear-resistant implant materials to improve the durability of the prosthesis and reduce the negative impressions of re-surgery and implant replacement in patients, as well as reducing the costs. In this regard, several studies have been performed to design and process implant materials with aim of improving their mechanical and biological properties. In particular, studies have been done on the synthesis of polymer and polymer composites for artificial bone applications and treatment of osteoarthritis. However, the application of these polymers is to some extent limited with their long-term biocompatibility and direct interaction with body cells and organs. Additionally, use of ceramics like alumina and zirconia as an implant material was examined for joint replacement; however, their application was limited due to brittleness, prostheses failure, and squeaking.

Alternatively, metallic joint prostheses (metal-on-metal) enjoy several merits, e.g., high wear resistance, straightforward mouldability, and shape flexibility. However, the application of metallic implants is extensively limited by the available synergy between interfacial corrosion and wear. Frequently, these effects lead to the formation of metallic debris and subsequent local inflammation, which might cause the loosening of prosthesis and injury in the implant area. To overcome these challenges, new implant materials have been developed by combination of biomedical grades of metallic substrates like stainless steel and cobalt-chromium alloys with polymers. While this effort has enabled promising implant substances with improved corrosion resistance, the weak tribomechanical properties of polymers remains a challenge.

To further increase the scope of polymer implants, strategies of polymer-carbon composites have emerged and shown to possess close natural bone stiffness, compared to metallic devices. Polymer-carbon composites most frequently contain ultra-high molecular weight polyethylene, PEEK, and polymethyl methacrylate in their matrices. These polymers have robust production and have shown good biocompatibility with human and animal cells. However, the tribological and mechanical properties of the polyethylene-based knee implants need to be significantly reinforced to prevent in-situ debris contamination while maintaining their biocompatibility. A study by Jacobs et al. examined the wear rate/volume of polyethylene implant material and reported the importance of tribology behavior as central factor in osteolytic potential and implant failure. In other studies, the synthesis of PEEK-carbon fiber composites reported superior properties of this material, compared to conventional polyethylene.

Numerous studies have been performed to investigate the tribological properties of alternative polymers/composites, such as PEEK and chopped carbon-fiber reinforced PEEK (CCFR-PEEK) in simulated body fluid and bovine serum. Despite the high capability of CCFR-PEEK for polymer-on-metal joint implant applications in these studies, further biocompatibility and toxicity analyses are required for using this alternative material for knee replacement configuration since the toxicity of carbon fibers has been recently verified.

Despite advances in artificial joint materials research, there is still a scarcity of composites that are biocompatible and nontoxic, that possess required tribological and mechanical properties, that are resistant to corrosion, and that have long lifetimes without failure, squeaking, and/or brittleness. These needs and other needs are satisfied by the present disclosure.

SUMMARY

Disclosed herein are MXene-aromatic thermosetting copolyester (ATSP) nanocomposites. In one aspect, the nanocomposites can be used to fabricate and/or coat artificial bone implants. In another aspect, the nanocomposites are biocompatible and/or nontoxic. Implants and coatings formed from the nanocomposites possess excellent compressive strength, hardness, and wear resistance in synovial fluid when compared to current implant coatings and materials.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figures 1A, 1B, 1C, 1D, 1E, 1F, 1G, 1H, 1I, 1J, 1K, 1L:
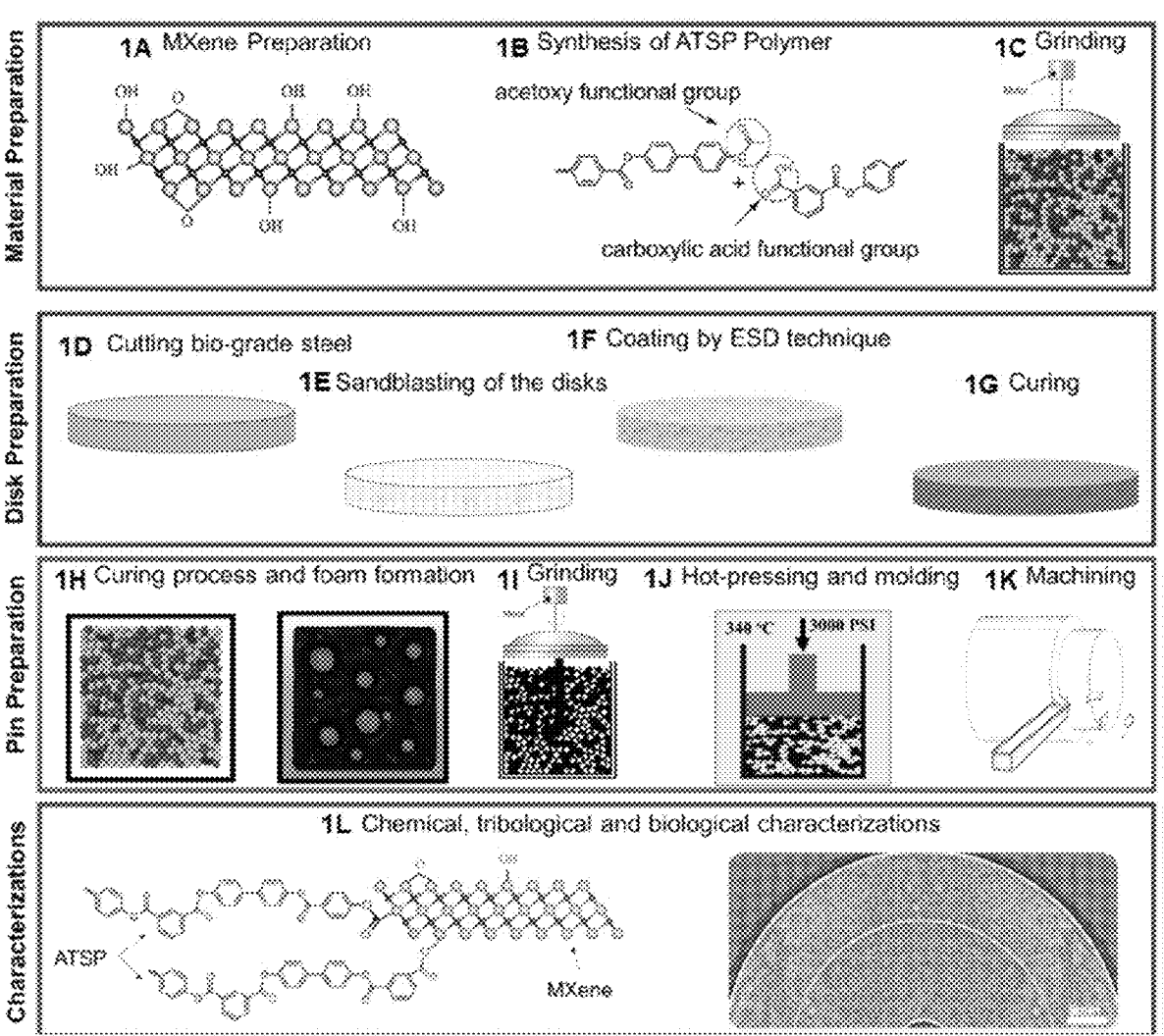
FIGS. 1A-1L show a schematic illustration of (FIGS. 1A-1C) material synthesis, preparation of (FIGS. 1D-1G)
Figures 2A, 2B, 2C, 2D, 2E, 2F:
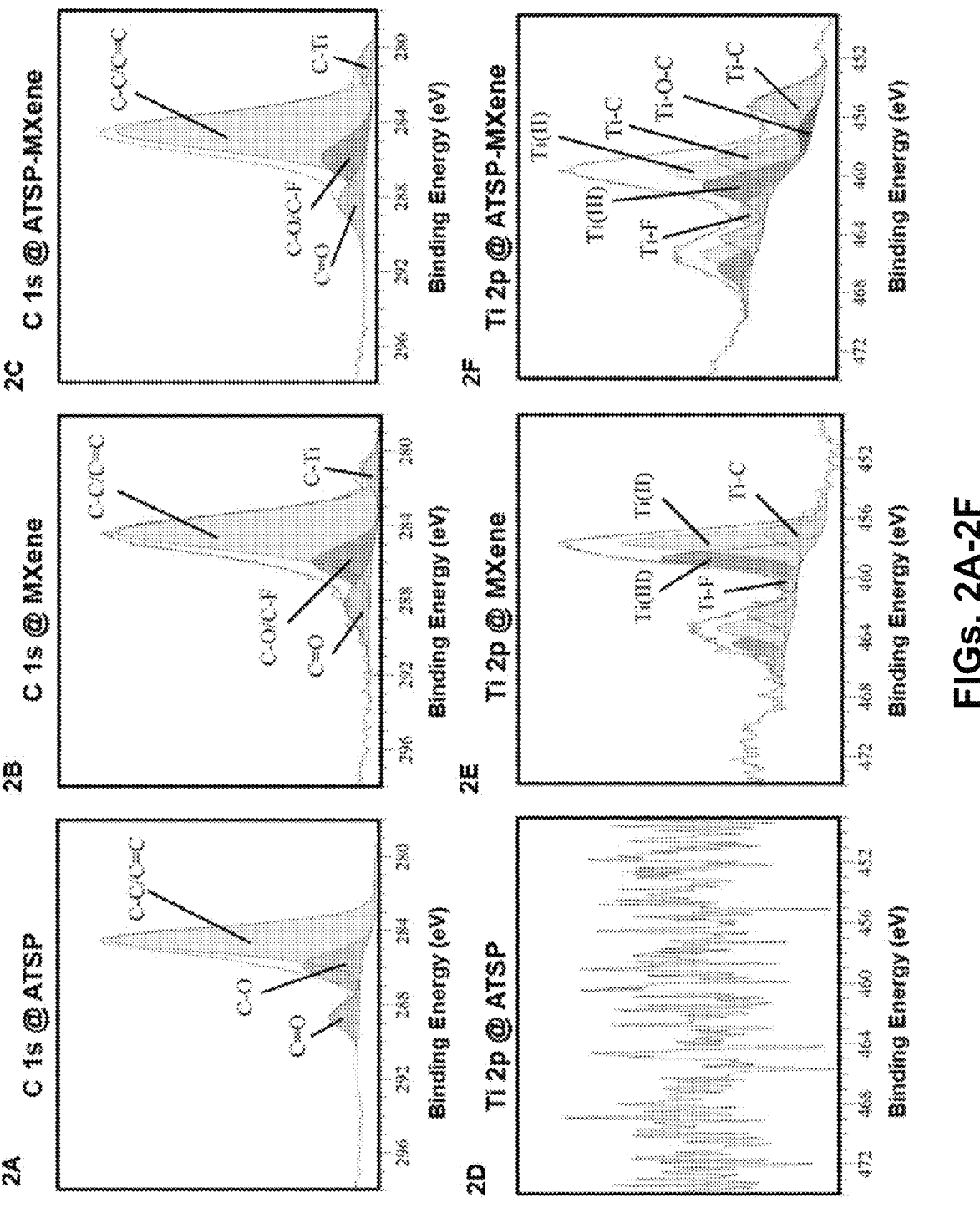

disks and (FIGS. 1H-1K) pins with the ATSP-MXene. The proposed chemical reactions between terminal groups on MXene and ATSP oligomers during curing process to synthesize ATSP-MXene is provided in FIG. 1L.

FIGS. 2A-2F show high-resolution C 1s XPS spectra for (FIG. 2A) Neat ATSP, (FIG. 2B) MXene, and (FIG. 2C) ATSP-MXene. High-resolution Ti 2p XPS spectra for (FIG. 2D) Neat ATSP, (FIG. 2E) MXene, and (FIG. 2F) ATSP-MXene.

Figure 3:
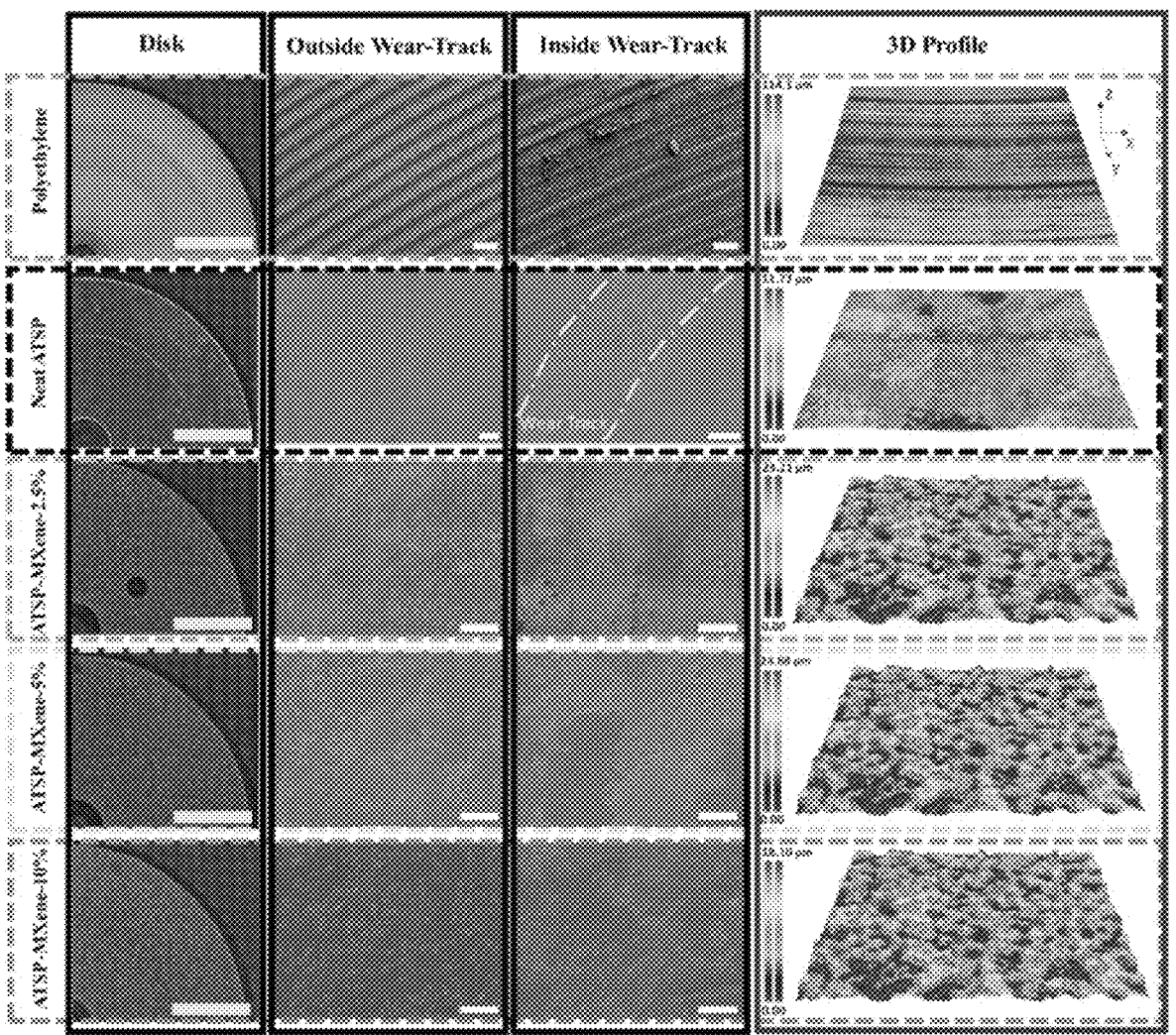

FIG. 3 shows optical images, SEM images, and 3D profiles of the polyethylene disks and disks coated by neat ATSP and ATSP-MXene disks with different percentages of MXene reinforcement. Yellow scale bars on optical images are 10 mm. White scale bars on SEM images are 100 µm.

Figure 4A:
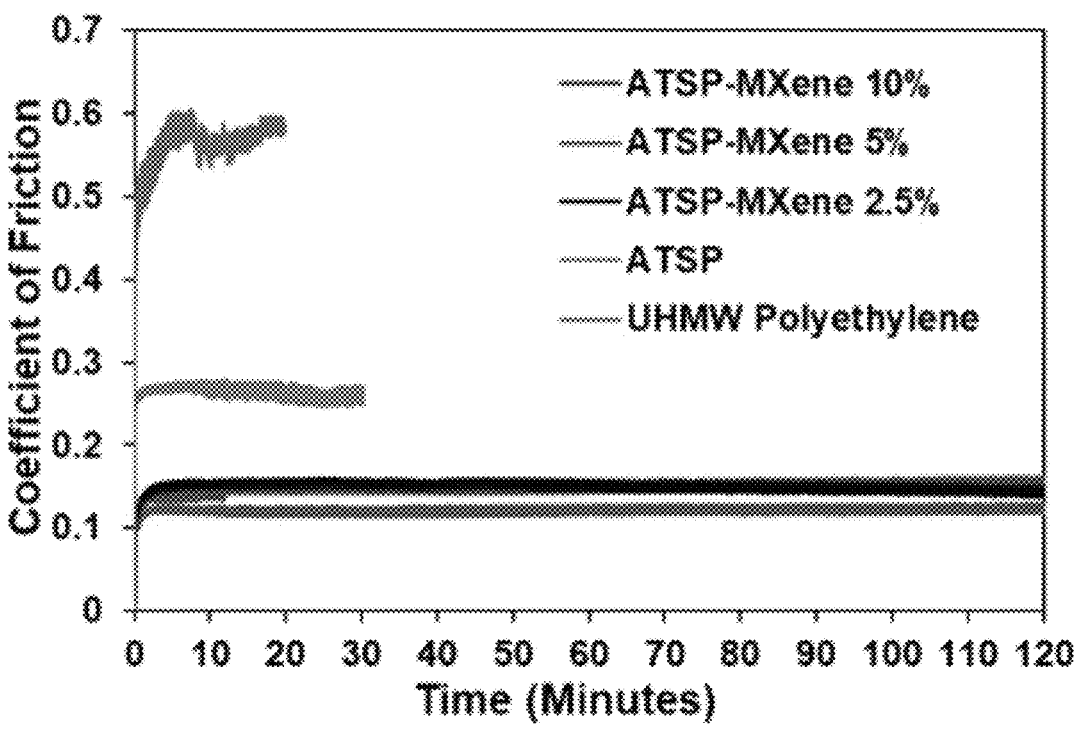

FIG. 4A shows in-situ COF as a function of time for different joint implants: ATSP, ATSP-MXene 2.5 wt % ATSP-MXene 5 wt %, ATSP-MXene 10 wt %, and when ATSP-MXene 5 wt % coated on bio-grade steel disks. (FIG. 4B) Average COF and (FIG. 4C) average wear rate results associated with different tribocouples. (FIG. 4D) Compressive force-displacement curve and (FIG. 4E) nanoindentation load-displacement curves of 5 wt % ATSP-MXene. (Inset) Hardness, H, and reduced modulus, Er, of the 5 wt % ATSP-MXene sample.

FIGS. 5A-5E show LIVE/DEAD viability and LDH cytotoxicity bioassays polyethylene, ATSP, and ATSP-MXene (5 wt %) fibers after co-culture with rat MSCs for 1 and 5 days.

Figure 6:
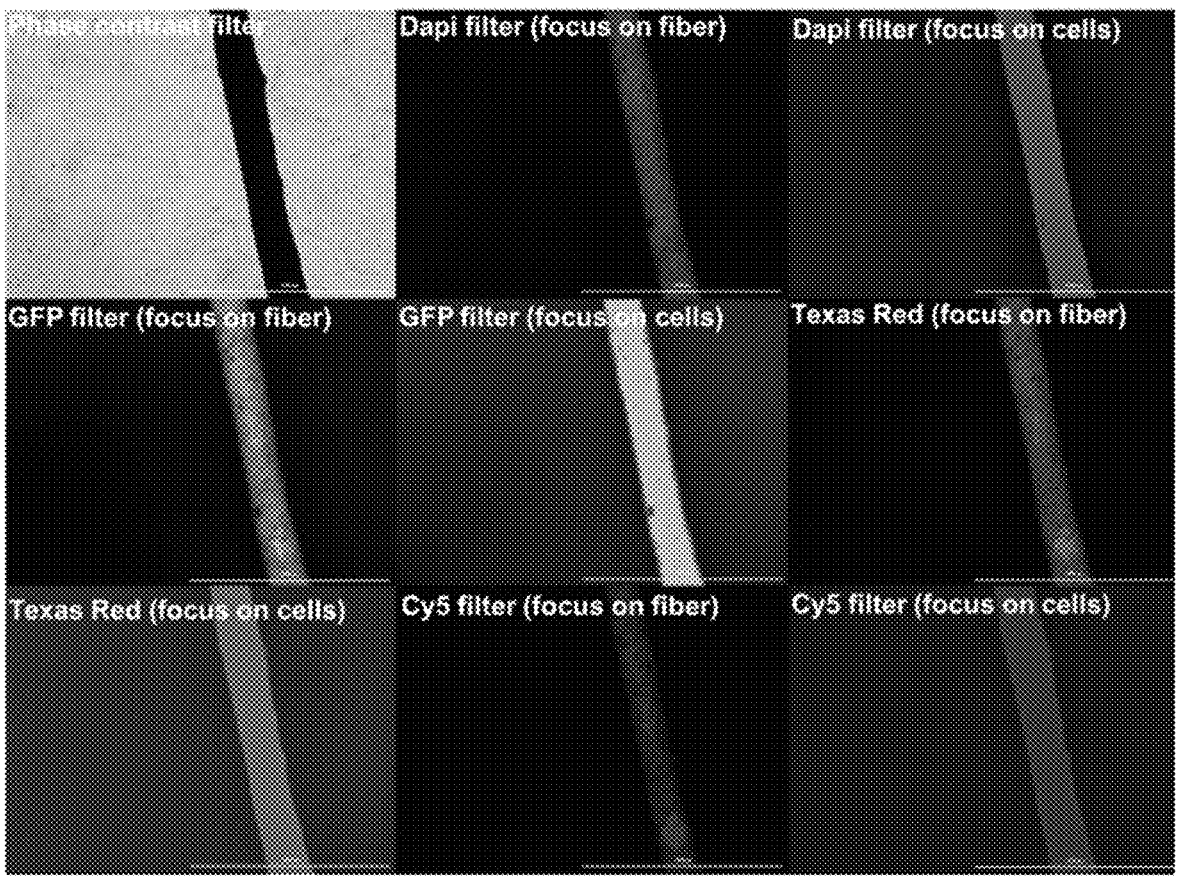

FIG. 6 shows auto-fluorescent properties of ATSP-MXene (5 wt %) at different excitation/emission ranges at day 5 of co-culture with rat MSCs.

Figure 7:
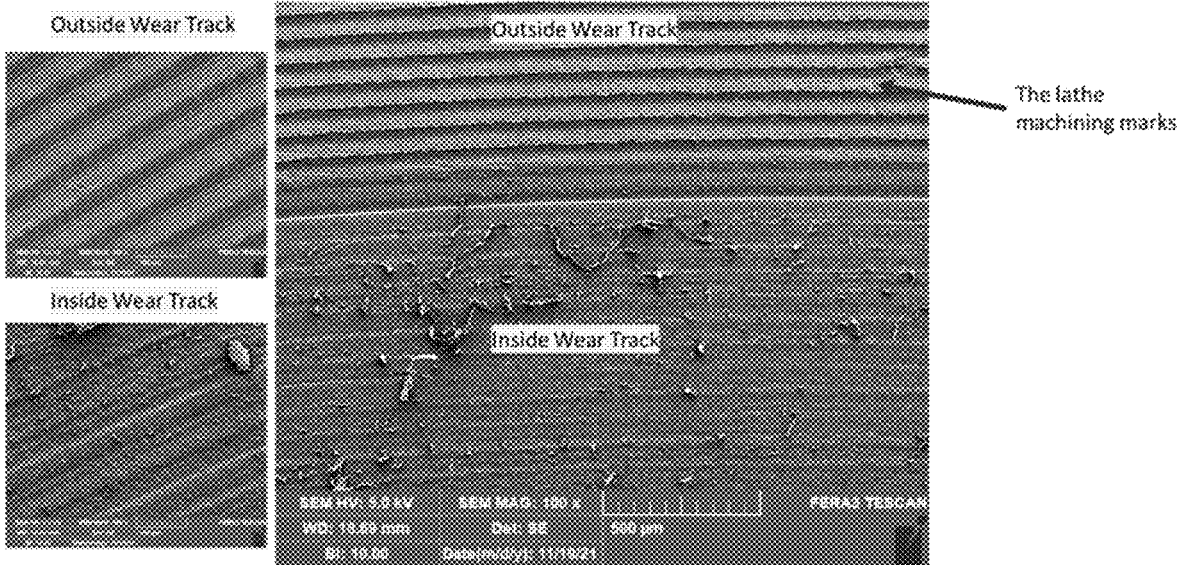

FIG. 7 shows SEM images of polyethylene pin on polyethylene disk (polyethylene on polyethyelene).

Figure 8:
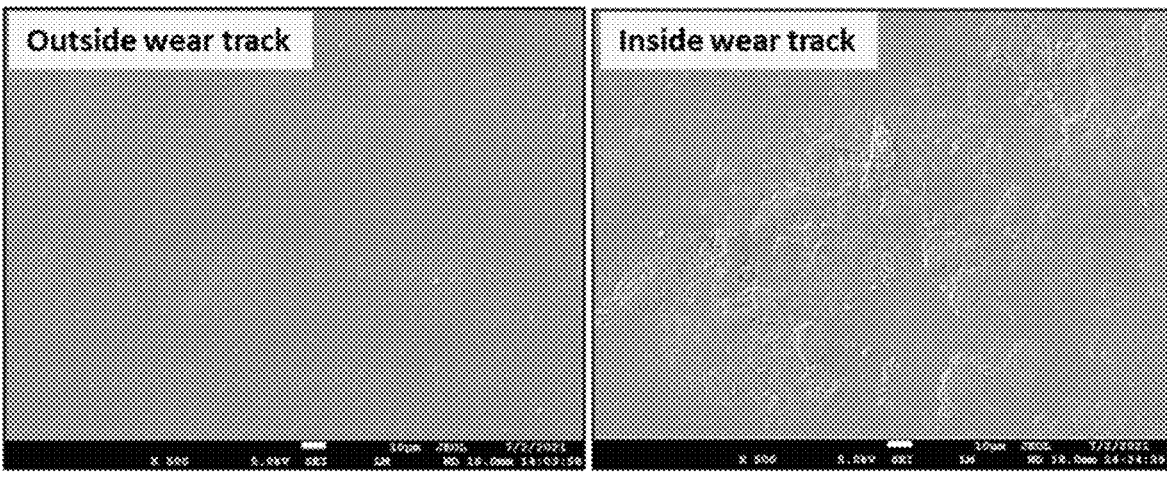

FIG. 8 shows SEM images of ATSP pin on ATSP-coated disk (ATSP on ATSP).

Figure 9:
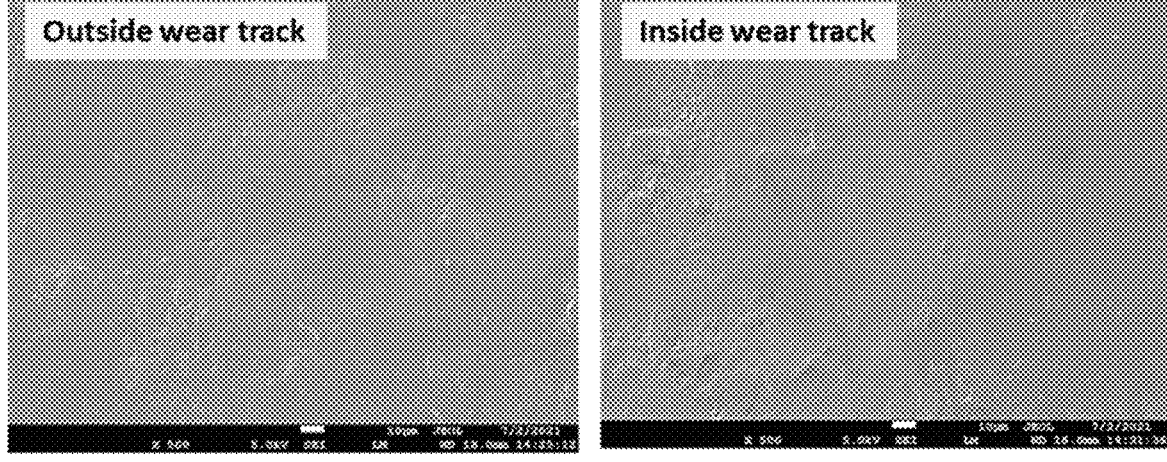

FIG. 9 shows SEM images of 2.5% ATSP-MXene pin on 2.5% ATSP-MXene-coated disk (ATSP-MXene on ATSP-MXene).

Figure 10:
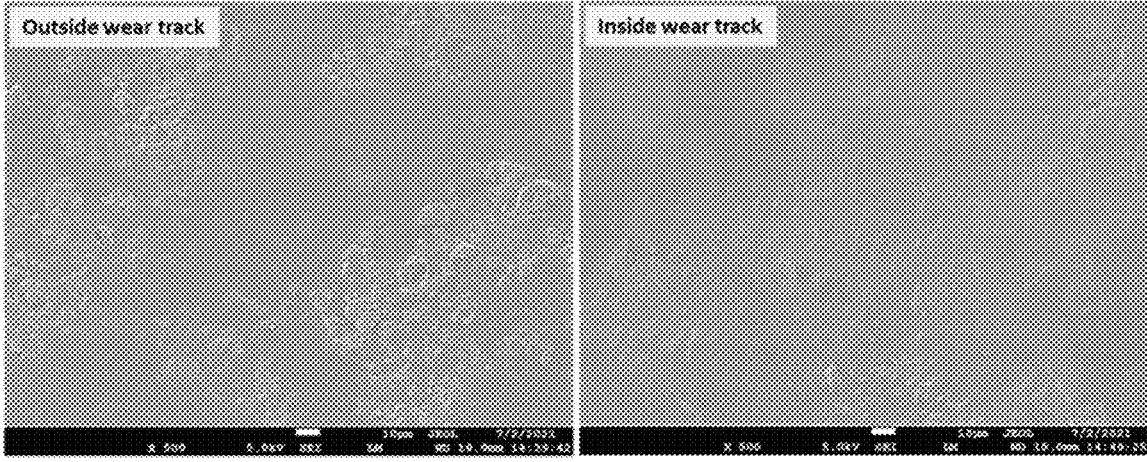

FIG. 10 shows SEM images of 5% ATSP-MXene pin on 5% ATSP-MXene-coated disk (ATSP-MXene on ATSP-MXene).

Figure 11:
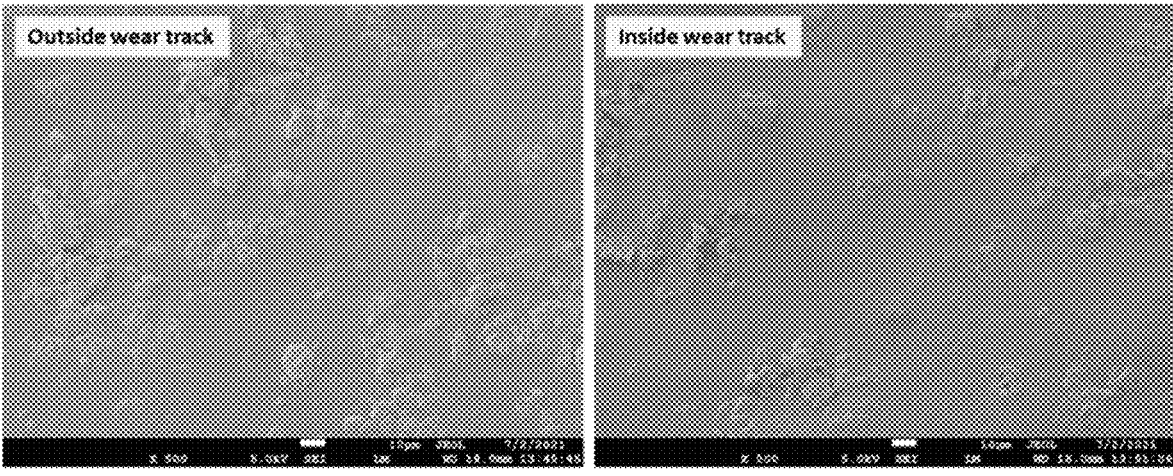

FIG. 11 shows SEM images of 10% ATSP-MXene pin on 10% ATSP-MXene-coated disk (ATSP-MXene on ATSP-MXene).

Figure 12A:
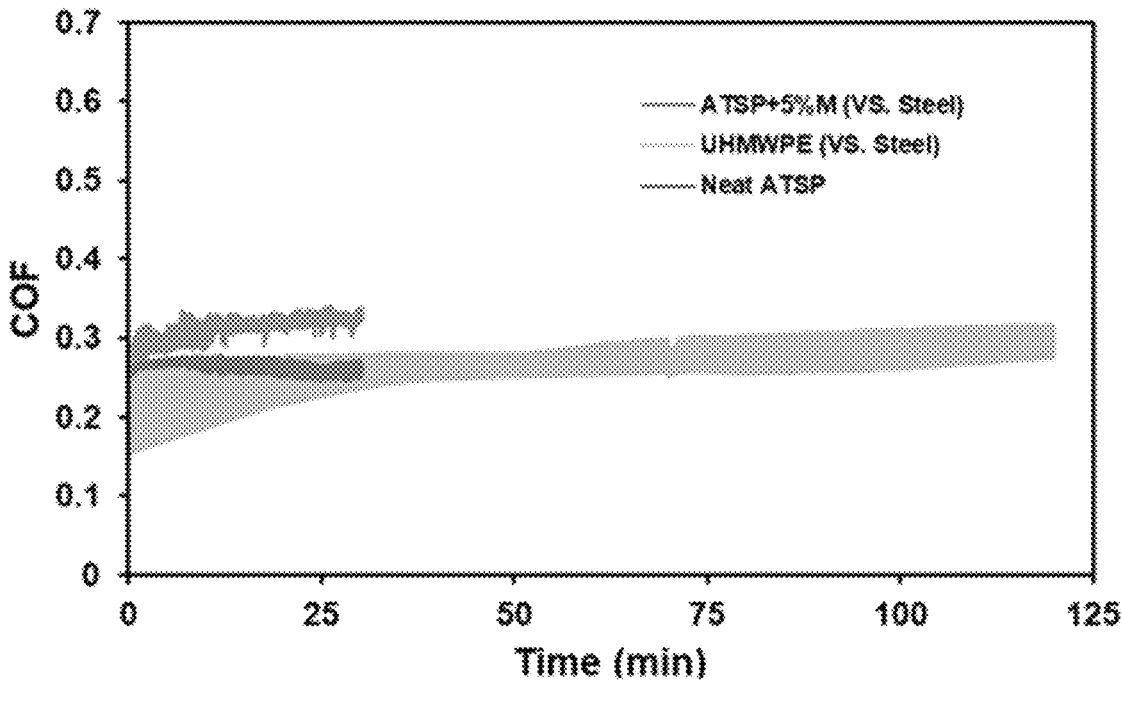
Figure 12B:
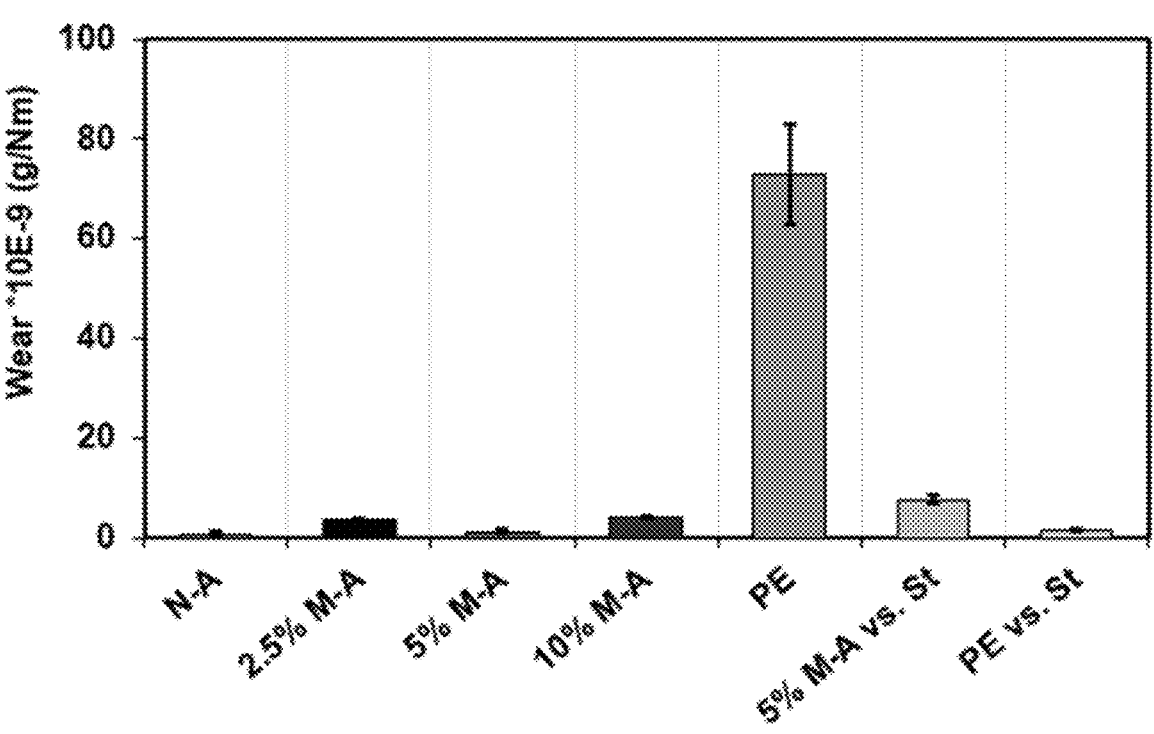
Figure 12C:
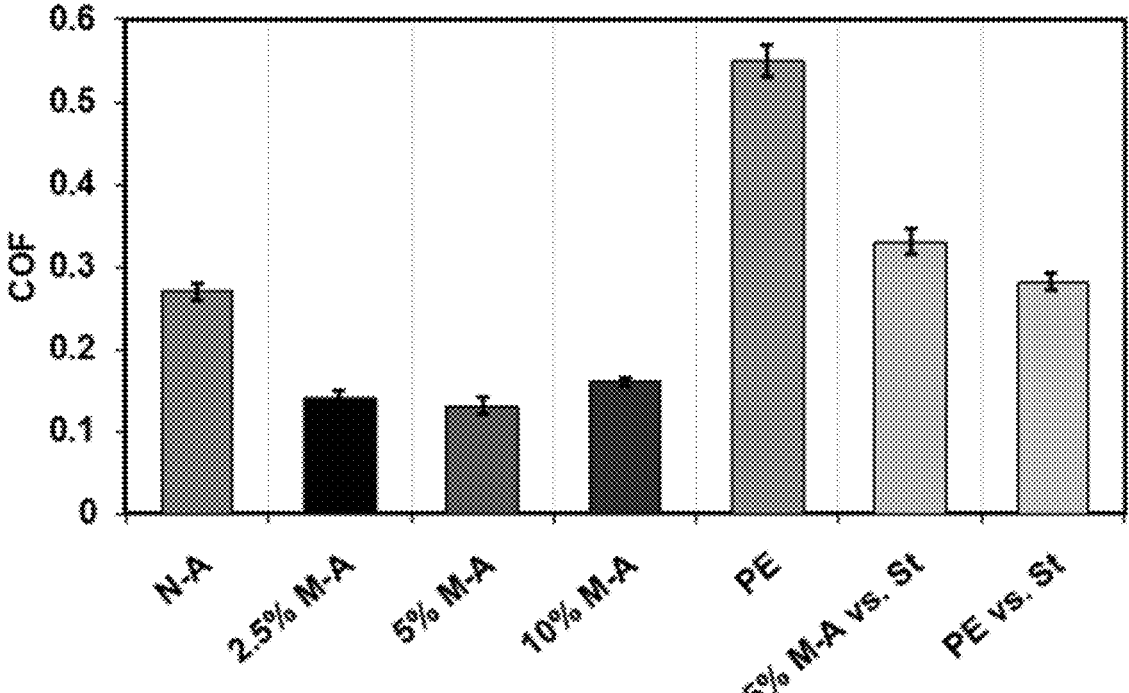

FIG. 12A shows in-situ COF as a function of time for different joint implants: Neat ATSP on Neat ATSP, Neat ATSP on stainless steel, and polyethylene on stainless steel (FIG. 12B) Average COF and (FIG. 12C) average wear rate results associated with different tribocouples including stainless steel.

Figure 13:
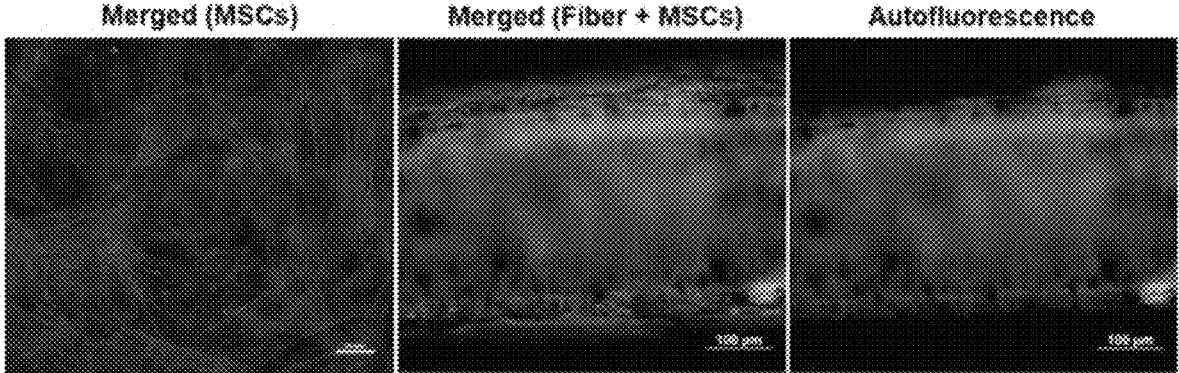
Figure 13:
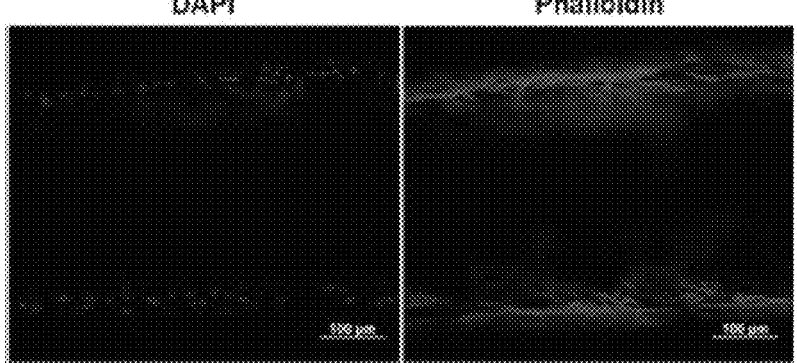

FIG. 13 shows demonstration of skeleton structure and morphology of fixed rat MSCs co-after 72 h of co-culture with ATSP-MXene specimens. Images were captured on a Nikon Eclipse Ti2-E fluorescence microscope at 90× and 30× magnifications on the MSCs and MSCs-treated specimens, respectively. Autofluorescence, GFP Filter; DAPI, DAPI Filter; Phalloidin, Cy7 Filter. These results show no significant change in the morphology of the treated cells, compared to the control group.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

In one aspect, disclosed herein is a new class of biocompatible composite materials, which can be used in coating and bulk form, with outstanding mechanical and tribological properties to be used as bearing bio-compatible materials. In a further aspect, ATSP is an emerging family of high-performance thermosetting polymers that chemically cross-links at high temperatures (>300° C.). In a still further aspect, the unique combination of properties such as bio-compatibility, dramatically high wear resistance, extremely high creep resistance, high mechanical properties such as Young's modulus, strength, and high corrosion resistance in both acidic and alkaline media, make these materials uniquely qualified as a platform to develop a unique high-performance joint implant. In one aspect, this new family of materials includes low wear, low coefficient of friction (COF) ATSP and transition metal carbide MXenes. In another aspect, as a novel promising biomaterial alternative for orthopedic implant applications, the tribological properties of the unreinforced (neat) and ATSP-MXene composites in simulated body fluid medium display superior performance when coated on steel implant substrate in synovial fluid, when investigated against ATSP and a bio-grade 316L stainless steel.

In one aspect, disclosed herein is a medical implant containing an aromatic thermosetting copolyester. In another aspect, the medical implant further includes MXene fillers. In one aspect, the aromatic thermosetting copolyester and MXene are processed into a composite material prior to forming the medical implant.

In one aspect, the MXene is present at from about 0.1 wt % to about 10 wt % relative to the aromatic thermosetting copolyester, or about 0.1, 0.25, 0.5, 0.75, 1, 2, 3, 4, 5, 6, 7, 8, 9, or about 10 wt %, or a combination of any of the foregoing values, or a range encompassing any of the foregoing values.

In another aspect, the medical implant can be a screw, pin, plate, mesh, valve, fiber, artificial joint, dental implant, or stabilizing device. In a further aspect, when the implant is an artificial joint, it can be a ball and socket joint, saddle joint, hinge joint, pivot joint, gliding joint, condyloid joint, or any combination thereof. In a still further aspect, the artificial joint can be a hip joint, a knee joint, a temporomandibular joint, a shoulder joint, an ankle joint, a finger joint, or an elbow joint. In one aspect, the stabilizing device can be a spinal implant.

In any of these aspects, the aromatic thermosetting copolyester or the composite material comprises a coating on a second material. In an aspect, the coating can be from about 10 to about 120 µm, or can be about 10, 15, 20, 25, 30, 35, 40, 45, 50, 55, 60, 65, 70, 75, 80, 85, 90, 95, 100, 105, 110, 115, or about 120 µm, or a combination of any of the foregoing values, or a range encompassing any of the foregoing values.

In one aspect, the second material can be stainless steel, a ceramic, titanium or a titanium alloy, polyethylene, neat ATSP, polyether ether ketone (PEEK), a cobalt-chromium alloy, another medical grade implant material, or any combination thereof.

In one aspect, the aromatic thermosetting copolyester or the composite material is coated onto the second material. In one aspect, coating can be achieved by spray coating, knife coating, dip coating, another coating method, or any combination thereof. In still another aspect, at least two contacting surfaces of the medical implant include the aromatic thermosetting copolyester or the composite material. In one aspect, the aromatic thermosetting copolyester or the composite material forms a three dimensional structure.

In one aspect, the aromatic thermosetting copolyester is a random copolymer comprising crosslinked oligomers, wherein the oligomers comprise two or more monomers. In another aspect, the two or more monomers can be selected from trimesic acid (TMA), 4-acetoxybenzoic acid (ABA), isophthalic acid (IPA), biphenol diacetate (BPDA), or any combination thereof. In still another aspect, the oligomers can have molecular weights of from about 400 kDa to about 2000 kDa, or of about 400, 500, 600, 700, 800, 900, 1000, 1100, 1200, 1300, 1400, 1500, 1600, 1700, 1800, 1900, or about 2000 kDa, or a combination of any of the foregoing values, or a range encompassing any of the foregoing values.

In one aspect, the two or more monomers can be present in numerous different ratios in the disclosed coatings and compositions. In one aspect, a first monomer and a second monomer can be present in a ratio of from about 7:1 to about 1:7, or at about 7:1, 6:1, 5:1, 4:1, 3:1, 2:1, 1:1, 1:2, 1:3, 1:4, 1:5, 1:6, or about 1:7, or a combination of any of the foregoing values, or a range encompassing any of the foregoing values. In some aspects, the first monomer or the second monomer can be absent and all or a portion of the oligomers can be polymers rather than copolymers.

In some aspects, the medical implant can further include an additive such as, for example, $MoS_2$, graphene, polytetrafluoroethylene (PTFE), another additive, or any combination thereof.

In another aspect, the MXene has the formula $Ti_3C_2T_x$, where $T_x$ represents one or more terminal groups. In another aspect, the terminal group can be selected from —OH, —COOH, —O, —F, or any combination thereof.

In one aspect, the medical implant is biocompatible. In another aspect, the medical impact, the coating, if present, or both are wear resistant.

In one aspect, the medical implant has a wear rate of from about $0.89×10^{-9}$ g/Nm to about $1.3×10^{-9}$ g/Nm, or about 0.89, 0.9, 1.0, 1.1, 1.2, or about $1.3×10^{-9}$ g/Nm, or a combination of any of the foregoing values, or a range encompassing any of the foregoing values. In another aspect, the medical implant has a compressive strength of from about 130 MPa to about 300 MPa, or of about 130, 150, 175, 200, 225, 250, 275, or about 300 MPa, or a combination of any of the foregoing values, or a range encompassing any of the foregoing values.

In one aspect, the medical implant has a reduced modulus of from about 2.8 GPa to about 4.8 GPa, or of about 2.8, 3, 3.2, 3.4, 3.6, 3.8, 4.0, 4.2, 4.4, 4.6, or about 4.8 GPa, or a combination of any of the foregoing values, or a range encompassing any of the foregoing values. In one aspect, the medical implant has a hardness of from about 0.2 GPa to about 0.3 GPa, or of about 0.2, 0.21, 0.22, 0.23, 0.24, 0.25, 0.26, 0.27, 0.28, 0.29, or about 0.3 GPa, or a combination of any of the foregoing values, or a range encompassing any of the foregoing values. In still another aspect, the medical implant has a coefficient of friction of from about 0.1 to about 0.25, or of about 0.1, 0.125, 0.15, 0.175, 0.2, 0.225, or about 0.25, or a combination of any of the foregoing values, or a range encompassing any of the foregoing values.

Also disclosed herein is a method for making a composite material that includes an aromatic thermosetting copolyester and an MXene, the method including at least the following steps:

(a) curing a mixture of one or more ATSP precursor powders and one or more MXenes to produce a first cured material;
(b) grinding the first cured material to form a second powder;
(c) curing the second powder to form a second cured material; and
(d) grinding the second cured material to form a final powder form.

In another aspect, the method further includes molding the final powder form into a solid bulk composite. In one aspect, molding can be conducted under a pressure of from about 10 MPa to about 41 MPa, or at about 10, 15, 20, 25, 30, 35, 40, or about 41 MPa, or a combination of any of the foregoing values, or a range encompassing any of the foregoing values. In another aspect, molding is carried out at a temperature of from about 340° C. to about 360° C., or at about 340, 342, 344, 346, 348, 350, 352, 354, 356, 358, or about 360° C., or a combination of any of the foregoing values, or a range encompassing any of the foregoing values.

In a further aspect, steps (a) and (c) can be accomplished at from about 260° C. to about 340° C., or at about 260, 265, 270, 275, 280, 285, 290, 295, 300, 305, 310, 315, 320, 325, 330, 335, or about 340° C., or a combination of any of the foregoing values, or a range encompassing any of the foregoing values. In another aspect, curing can be carried out in an oven, by infrared (IR) heating, by laser heating, or, if a microwave absorbing material is present in the composition, using microwave heating. In one aspect, curing is carried out in an oven at about 330° C. In one aspect, when a composite coating is used, the cure temperature can be from about 260° C. to about 330° C. In an alternative aspect, when a bulk composite material is used, the cure temperature can be from about 300° C. to about 340° C. In any of these aspects, the one or more ATSP precursor powders include a monomer having carboxylic acid terminal groups, a monomer having acetoxy terminal groups, or any combination thereof.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a polymer," "an MXene," or "a coating," includes, but is not limited to, mixtures or combinations of two or more such polymers, MXenes, coatings, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g., the phrase "x to y" includes the range from "x" to "y" as well as the range greater than "x" and less than "y." The range can also be expressed as an upper limit, e.g., "about x, y, z, or less" and should be interpreted to include the specific ranges of "about x," "about y," and "about z" as well as the ranges of "less than x," "less than y," and "less than z." Likewise, the phrase "about x, y, z, or greater" should be interpreted to include the specific ranges of "about x," "about y," and "about z" as well as the ranges of "greater than x," "greater than y," and "greater than z." In addition, the phrase "about 'x' to 'y'," where "x" and "y" are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of an MXene refers to an amount that is sufficient to achieve the desired improvement in the property modulated by the component. The specific level in terms of wt % in a composition required as an effective amount will depend upon a variety of factors including the amount and type of polymers used to form a composite with the MXene, whether the composite is to be used as a coating or a molded device, and location in the body in which a device including the composite is to be implanted.

As used herein, the terms "optional" or "optionally" means that the subsequently described event or circumstance can or cannot occur, and that the description includes instances where said event or circumstance occurs and instances where it does not.

Unless otherwise specified, pressures referred to herein are based on atmospheric pressure (i.e., one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The present disclosure can be described in accordance with the following numbered Aspects, which should not be confused with the claims.

Aspect 1. A medical implant comprising an aromatic thermosetting copolyester (ATSP).

Aspect 2. The medical implant of aspect 1, wherein the implant further comprises an MXene.

Aspect 3. The medical implant of aspect 2, wherein the aromatic thermosetting copolyester and the MXene are processed into a composite material prior to forming the medical implant.

Aspect 4. The medical implant of aspect 3, wherein the MXene is present at from about 0.1 wt % to about 10 wt % relative to the aromatic thermosetting copolyester.

Aspect 5. The medical implant of any one of aspects 1-4, wherein the medical implant comprises a screw, a pin, a plate, a mesh, a valve, a fiber, an artificial joint, a dental implant, or a stabilizing device.

Aspect 6. The medical implant of aspect 5, wherein the artificial joint comprises a ball and socket joint, a saddle joint, a hinge joint, a pivot joint, a gliding joint, a condyloid joint, or any combination thereof.

Aspect 7. The medical implant of aspect 5, wherein the artificial joint comprises a hip joint, a knee joint, a temporomandibular joint, a shoulder joint, an ankle joint, a finger joint, or an elbow joint.

Aspect 8. The medical implant of aspect 5, wherein the stabilizing device comprises a spinal implant.

Aspect 9. The medical implant of any one of aspects 1-8, wherein the aromatic thermosetting copolyester or the composite material comprises a coating on a second material.

Aspect 10. The medical implant of aspect 9, wherein the coating has a thickness of from about 10 to about 120 μm.

Aspect 11. The medical implant of aspect 9 or 10, wherein the second material comprises stainless steel, a ceramic, titanium or a titanium alloy, polyethylene, neat ATSP, polyether ether ketone (PEEK), a cobalt-chromium alloy, another medical grade implant material, or any combination thereof.

Aspect 12. The medical implant of any one of aspects 9-11, wherein the aromatic thermosetting copolyester or the composite material is coated onto the second material.

Aspect 13. The medical implant of any one of aspects 5-12, wherein at least two contacting surfaces of the medical implant comprise the aromatic thermosetting copolyester or the composite material.

Aspect 14. The medical implant of any one of aspects 1-13, wherein the aromatic thermosetting copolyester or the composite material comprises a three dimensional structure.

Aspect 15. The medical implant of any one of aspects 1-14, wherein the aromatic thermosetting copolyester comprises a random copolymer comprising crosslinked oligomers, wherein the oligomers comprise two or more monomers.

Aspect 16. The medical implant of aspect 15, wherein the two or more monomers comprise trimesic acid (TMA), 4-acetoxybenzoic acid (ABA), isophthalic acid (IPA), biphenol diacetate (BPDA), or any combination thereof.

Aspect 17. The medical implant of aspect 15 or 16, wherein the oligomers have molecular weights of from about 400 to about 2000 kDa.

Aspect 18. The medical implant of any one of aspects 1-17, further comprising an additive.

Aspect 19. The medical implant of aspect 18, wherein the additive comprises $MoS_2$, graphene, polytetrafluoroethylene (PTFE), another additive, or any combination thereof.

Aspect 20. The medical implant of any one of aspects 2-19, wherein the MXene has the formula $Ti_3C_2T_x$, wherein $T_x$ comprises one or more terminal groups.

Aspect 21. The medical implant of aspect 20, wherein the one or more terminal groups comprise —OH, —COOH, —O, —F, or any combination thereof.

Aspect 22. The medical implant of any one of aspects 1-21, wherein the medical implant is biocompatible.

Aspect 23. The medical implant of any one of aspects 1-22, wherein the medical implant, the coating if present, or both, are wear-resistant.

Aspect 24. The medical implant of any one of aspects 1-23, wherein the medical implant has a compressive strength of from about 130 MPa to about 300 MPa.

Aspect 25. The medical implant of any one of aspects 1-24, wherein the medical implant has a reduced modulus of from about 2.8 GPa to about 4.8 GPa.

Aspect 26. The medical implant of any one of aspects 1-25, wherein the medical implant has a hardness of from about 0.2 GPa to about 0.3 GPa.

Aspect 27. The medical implant of any one of aspects 1-26, wherein the medical implant has a coefficient of friction of from about 0.1 to about 0.25.

Aspect 28. A method for making a composite material comprising an aromatic thermosetting copolyester and an MXene, the method comprising:

(a) curing a mixture of one or more ATSP precursor powders and one or more MXenes to produce a first cured material;

(b) grinding the first cured material to form a second powder;

(c) curing the second powder to form a second cured material; and (d) grinding the second cured material to form a final powder form.

Aspect 29. The method of aspect 28, further comprising molding the final powder form into a solid bulk composite.

Aspect 30. The method of aspect 29, wherein molding is conducted under a pressure of from about 10 MPa to about 41 MPa.

Aspect 31. The method of aspect 29 or 30, wherein molding is carried out at a temperature of from about 340° C. to about 360° C.

Aspect 32. The method of any one of aspects 28-31, wherein steps (a) and (c) are accomplished in an oven at from about 260° C. to about 340° C.

Aspect 33. The method of any one of aspects 28-32, wherein curing is accomplished in an oven, by infrared (IR) heating, by laser heating, or using microwave heating.

Aspect 34. The method of any one of aspects 28-33, wherein the one or more ATSP precursor powders comprise a monomer having carboxylic acid terminal groups, a monomer having acetoxy terminal groups, or any combination thereof.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

Synthesis of the $Ti_3C_2T_x$ MXene

The developed technique by Eom et al. was used for fabrication of the $Ti_3C_2T_x$ MXene from $Ti_3AlC_2$ MAX phase: 40 mL of HCl (9 M) and 2 g of lithium fluoride (LiF) were mixed for 0.5 h at 35° C. and followed by gradual addition of 2 gr MAX phase ($Ti_3AlC_2$) and mixing for 24 h under nitrogen atmosphere. After etching, the Al layer in the MAX phase was etched to exfoliate the $Ti_3C_2T_x$. The resulting suspension was diluted with deionized water and was subjected to several washing cycles using a centrifuge to remove the acidic impurities from MXene. As the pH reached about 6, the $Ti_3C_2T_x$ MXene sheets were placed in a vacuum oven at 50° C. for 24 h, followed by sealing with parafilm and storing at –25±5° C.

Synthesis of ATSP-MXene Composite

The precursor oligomers of ATSP resin, namely CB2 with carboxylic acid terminal groups and AB2 with acetoxy terminal groups were fabricated in a batch melt polymerization through mixing the biphenol diacetate, 4-acetoxybenzoic acid, isophthalic acid, trimesic acid, and hydroquinone diacetate (HQDA) monomers by heating to 270° C. under Argon atmosphere. The resultant oligomers were ground into powder after reaction and subsequently mixed at a mass ratio of 1:1 to synthesize CB2AB2 powder. The ATSP powders were subsequently blended with the given amount of $Ti_3C_2T_x$ ($T_x$: —OH, —O, and —F). The sandblasted corrosion-resistant 316L stainless steel disks were coated by ATSP/MXene using electrostatic spray deposition (ESD) technique and cured at 270° C. in a convective oven for 1 hr. The crosslinks formed by reaction between the terminal groups of the oligomers and between the end functional groups on oligomers' chains and MXene flakes. The possible reactions (crosslinking) between the two oligomers as well as oligomers and terminal groups on MXene flakes is shown in FIGS. 1A-1L. The thickness of the ATSP/MXene nanocomposites was 35±5 μm.

Fabrication of ATSP-MXene Coated Steel Disks

The biomedical grade corrosion-resistant 316L stainless steel plates were EDM wire cut to disks with a diameter of 5 cm and treated by sandblasting process to improve the adherence of the coating. The sandblasted disks were 3D coated by ATSP-MXene layers with an approximate thickness of 35 μm using powder electrostatic spray deposition (ESD) method and subjected to curing process in a convective oven at 270° C. for 1 hr. The crosslinking formed by the reactions between terminal groups available in the oligomers' structure and on the surface of oligomers' chains and MXene nanosheets.

Preparation of Polyethylene, ATSP, and ATSP-MXene Pins and Bio-Specimens

For fabrication of the pins, the resultant ATSP-CB2AB2 mixture in powder form was transferred into a mold and subjected to a heating process at 340° C. under 3000 PSI for 1 hr., followed by machining process to obtain the pins with specific dimensions.

To fabricate ATSP-MXene fibers for the biological studies, the resultant ATSP-CB2AB2 mixture in powder form were transferred into a twin-screw extruder at 270° C. and was subjected to a heating process for 10 minutes, followed by extruding through a die. All the parts of the extruders, e.g., screws, die, etc., were washed several times by ethanol to avoid any contamination. The final sample was directly cooled by a fan and transferred into a plastic bag without touching for the bio-based tests.

Tribological, Mechanical, Topographical, and Chemical Characterization

The tribological performance of the samples was evaluated with a pin-on-disk experimental configuration in a commercial tribometer (Rtec-Instruments). During experiments, the in-situ friction and normal forces were measured using a 2-axis load cell to calculate the in-situ COF. The experiments were performed with a unidirectional motion under lubricated sliding conditions. Simulated Body Fluid (SBF) was used as the lubricant medium with composition shown in Table 1. Each experiment was conducted under constant normal load of 100 N resulting in a nominal contact pressure of 3.54 MPa. The disk samples were rotated against the stationary pins for duration of 2 hr at a sliding speed of 54 rpm, equivalent to linear speed of 0.1 m/s. Before each experiment, the samples were immersed in isopropyl alcohol and cleaned for 10 min using an ultrasonic cleaner and subsequently rinsed with isopropyl alcohol, and dried using warm air. The samples were then placed in a desiccator to prevent any contamination. The same procedure was followed after each experiment.

After the experiments, the surface of the ATSP coated disks were imaged using a digital optical microscope to visually detect any wear scars at the macro scale. Scanning Electron Microscopy (SEM) images were obtained using an ultra-high-resolution FE-SEM (JEOL JSM-7500F) to visually depict the wear on the samples and investigate the corresponding wear mechanisms. The 3D surface topography of the coatings was obtained using a confocal microscope equipped with the tribometer. The surface profiles were then used to calculate the wear rate on the disk samples according to a literature procedure. The mass of each polymer pin was measured before and after each test using a scale with precision of 0.01 mg. Thereafter, the wear rate was calculated from the measured mass loss according to the following equation:

$$k = \frac{\Delta m}{L \cdot F_N}$$

where k, $\Delta m$, L, and $F_N$ are the wear rate in (g/Nm), the mass loss in (g), the total sliding distance in (m), and the applied normal load in (N), respectively.

We measured the wear scars using a Dektak Bruker profiler and the 3D profiles using a confocal microscope equipped with the tribometer. The Omicron X-ray photoelectron spectroscopy (XPS) device was used for chemical analysis. This device was equipped with an Argus detector with an excitation source of Mg Ka 1253.6 eV, and all the experiments were performed at the X-ray voltage of 15,000 and X-ray power of 300 W. The CN10 charge neutralizer was applied to minimize charging on samples. The aperture #3 was used with a rectangular shape to maximize the possible analysis area. The analysis of the obtained data was performed on CaseXPS software. Compression experiments were performed until sample failure using an Instron compression testing machine. The micromechanical properties (microhardness and reduced elastic modulus) of the ATSP-MXene composites were measured using an instrumented nanoindenter (TI Premier, Bruker) equipped with a high load Berkovich tip.

Sample Preparation for Biocompatibility Tests

Similar size of the extruded polyethylene, neat ATSP, and ATSP-MXene fibers were cut to pieces with an approximate length of 10 mm and exposed to UV light under laminar airflow for 60 minutes. The fibers were then soaked in 70% ethanol for 3-5 minutes followed by washing three times by phosphate-buffered saline (PBS, 1×) for sterilization, and stored at 4° C. for further experiments.

Cell Isolation

All animal protocols have been approved by the Animal Care Committee of the University of Manitoba (REB) and conform to the Guide for the Care and Use of Laboratory Animals by the US National Institutes of Health Publication (No. 85-23, revised 1985). Primary bone marrow mesenchymal stem cells (MSC) were flushed from the femur or tibia of adult Sprague-Dawley (SD) rats and cultured according to published protocols in low-glucose DMEM (10567014, Gibco) supplemented with 15% fetal bovine serum (FBS), 1:100 Penicillin-Streptomycin and 0.055 mM 2-mercaptoethanol. Adherent cells up to confluency of 80-90% were cultured for at least three passages before being used for experiments.

LIVE/DEAD Fluorescent Assay and Cytotoxicity Assessment

MSCs were plated in 96 well plates and allowed to grow for 24 hrs. Experimental samples prepared in section 2.4 were subsequently added to the wells for a 24-hr co-culture. Subsequently, fibers were removed and wells were washed with PBS. Assessment for cell viability was performed using a LIVE/DEAD Viability/Cytotoxicity Kit (L3224, Thermo Fisher Scientific, USA). Microplate readings were taken using a Cytation 5 Cell Imaging Multi-Mode Reader (BioTek Instruments, USA). MSCs were stained with Calcein (for live cells, green) and EthD-1 (for dead cells, red). Representative microscopy images were taken using a Nikon Eclipse Ti-2 Fluorescence Microscope (Nikon Instruments Inc., USA). To assess cytotoxicity effects, $5 \times 10^4$ rat's MSC were cultured in the defined media with fibers for 24 hrs using a lactate dehydrogenase (LDH) Kit (MK401, Cytotoxicity Detection Takara Bio) (n=5).

Autofluorescence Properties

The autofluorescence of fibers was detected by a fluorescence microscope (Cytation5) at different excitation/emission wavelengths including of DAPI (blue, 377 nm/447 nm), GFP (green, 469 nm/525 nm), Cy5 (red, 628 nm/685 nm), and Texas Red (orange, 586 nm/647 nm) filters.

Statistical Analysis

In the current study, the biological values were expressed as mean±standard deviation. A one-way ANOVA with Tukey's HSD or two-tailed Student's t-test was used. A statistically significant p-value of <0.05, <0.01, and <0.0001 were considered as *, , and **. All analyses performed using GraphPad Software (Prism, 8.0.1 La Jolla California USA).

Example 2: Results and Discussion

Morphology and Surface Chemistry

FIGS. 1A-1L depict the schematic model of the material synthesis and molecular structure of ATSP-MXene nanocomposite before and after curing processes. As it can be seen, the oligomers of ATSP were first synthesized, mixed with different concentrations of $Ti_3C_2T_x$ MXene to obtain a homogenous mixture powder with approximate mesh size of 40 μm. The obtained mixtures were separately coated on sandblasted bio-grade 316L steel to fabricate the disks. To fabricate pins as a tribo-couple element and for mechanical characterization, as schematically shown in FIGS. 1I-1L, the semi cured ATSP foam was ground, and molded again at 340° C. Then, the obtained sample was machined to the final pin shape. The final pin and disks were then analyzed elementally, mechanically, and tribologically.

The chemical structure of ATSP, $Ti_3C_2T_x$ MXene nanosheets and ATSP-MXene were studied by XPS analysis. FIGS. 2A-2F show the high-resolution C 1s spectra of the cured ATSP, MXene nanosheets, and ATSP-MXene composite after curing, respectively. The cured ATSP sample showed three peaks at ~284.5 eV, 286.0 eV, and 288.5 eV, corresponding to the sub-stoichiometric C—C/C=C, C—O, and C=O bonds, respectively. The high-resolution C 1s spectrum associated with MXene nanosheets was fitted with four components of C—Ti (~281.0 eV), C—C/C=C (~284.5 eV), C—O/C—F (~286.0 eV), and C=O (~288.5 eV). The C 1s spectrum of ATSP-MXene composite and MXene nanosheets illustrated the same functional compositions, including four components of C—Ti, C—C/C=C, C—O/C—F, and C=O. Considering the ATSP matrix, it was expected to observe a weaker C—Ti peak due to the dominant contribution of C—C bonds. Both ATSP-MXene and MXene nanosheets samples presented almost the same C—Ti content (around 4%), confirming the formation of further C—Ti bonds. This is in agreement with the literature.

While the Ti 2p spectra of ATSP displayed no peak, the Ti 2p peaks of MXene sheets and ATSP-MXene were compared, both of which comprised of $2p_{1/2}$ and $2p_{3/2}$ spin-orbit split components. In the case of MXene, the $2p_{1/2}$ and $2p_{3/2}$ spin-orbit split components can be fit with only four pairs of Gaussian-Lorentzian curves. Each pair component for the MXene consists of four pairs of distinguishable components at ~457 eV, 458 eV, 459 eV, and 460 eV for $2p_{3/2}$, which can be assigned to Ti—C, Ti(II) oxide, and Ti(III) oxide, and Ti—F, respectively.

After curing of the ATSP-MXene mixture on the bio-grade disk, all the peaks associated with MXene experienced a slight shift (1 eV) to higher binding. Simultaneously, two peaks of at the binding energy of 454.5 eV and 456.5 eV were respectively added, indicating the formation of Ti—C and Ti—O—C covalent bonding between ATSP and MXene nanosheets. Interestingly, the XPS data reveled the formation of new bond between MXene and ATSP.

FIG. 3 shows optical microscope and SEM images of the polyethylene, neat ATSP and ATSP-MXene coated disks after experiments. Optical and SEM images of polyethylene show a deep wear track after tribological tests, as shown in FIGS. 3 and 7. Outside the wear track or before subjecting the polyethylene sample to the test, there are some visible machining marks. The SEM images (FIG. 7) clearly show the activation of both adhesive and abrasive wear mechanism for the polyethylene case. While the neat ATSP showed a clear abrasive wear track after subjected to the tribological test, the wear associated with various ATSP-MXene samples with different MXene contents was extremely low and non-distinguishable from the images. The comparison of the outside and inside wear tracks in the SEM images clearly show the mild polishing effect, resulting from the reinforced 2D MXene fillers and the formation of strong covalent bonds between the terminal active groups on MXene and ATSP once curing.

Therefore, the wear was unmeasurable ("zero" wear) for all the ATSP-MXene coated disks as is also demonstrated from the wear scan measurements shown in FIGS. 3 and 8-11. On the other hand, the medical-grade polyethylene, as the most efficient material thus far, showed significantly high wear rate/wear depth (FIG. 7). This innovative idea addresses a solution for the main drawback of wear debris of polyethylene (UHMWPE) and its derivatives, the occurrence of periprosthetic osteolysis. 3D profiles of the neat ATSP and ATSP-MXene with different MXene contents are also shown in FIG. 3. Commonly, the roughness of the samples increases with the MXene content. However, the 3D surface topography of the ATSP-MXene composites, even as a thin film, showed no wear track other than slight abrasive wear for the Neat ATSP.

Tribological Performance

FIG. 4A illustrates the in-situ COF as a function of sliding time for different joint implant candidate materials: polyethylene, ATSP, ATSP-MXene 2.5 wt % ATSP-MXene 5 wt %, ATSP-MXene 10 wt %, and coated ATSP-MXene 5 wt % coated on bio-grade steel disks. The results were compared to the bio-grade polyethylene joint implants (FIG. 4A) and polyethylene on stainless joint implants (FIGS. 12A-12C) at the same conditions on the same figure. As clearly shown in FIGS. 4A and 12A-12C, the COF of the ATSP-MXene-based joint implants was significantly lower than the other tribo-pairs. This is attributed to the in-situ formation of Ti3C2Tx-nanosheets tribo-film on the sliding surface.

Figure 4B:
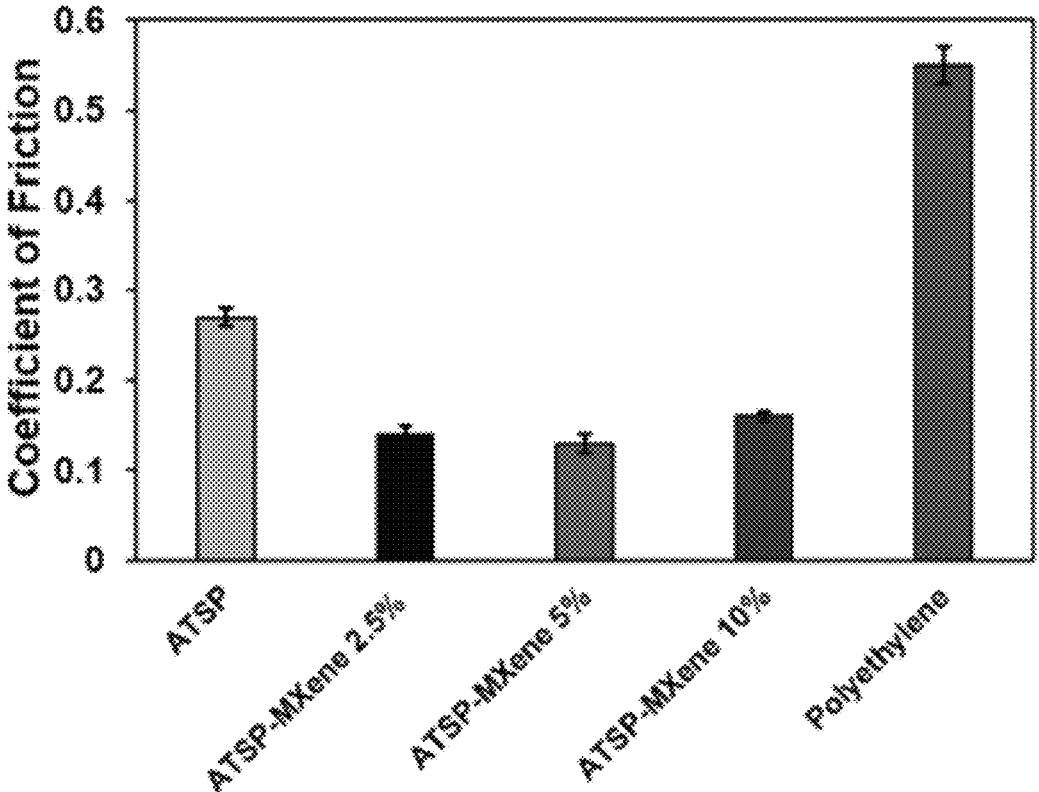

Among them, 5% ATSP-MXene showed the lowest average COF value of 0.12 (FIG. 4B). Dissimilar to polyethylene tribo-pairs, all ATSP-MXene-based joint implants showed stable and low COF for the duration of the experiments under the same operational conditions. The comparison of the average COF results associated with different tribo-pairs in FIG. 4B evidently shows the positive effect of MXene addition to the neat ATSP.

Figure 4C:
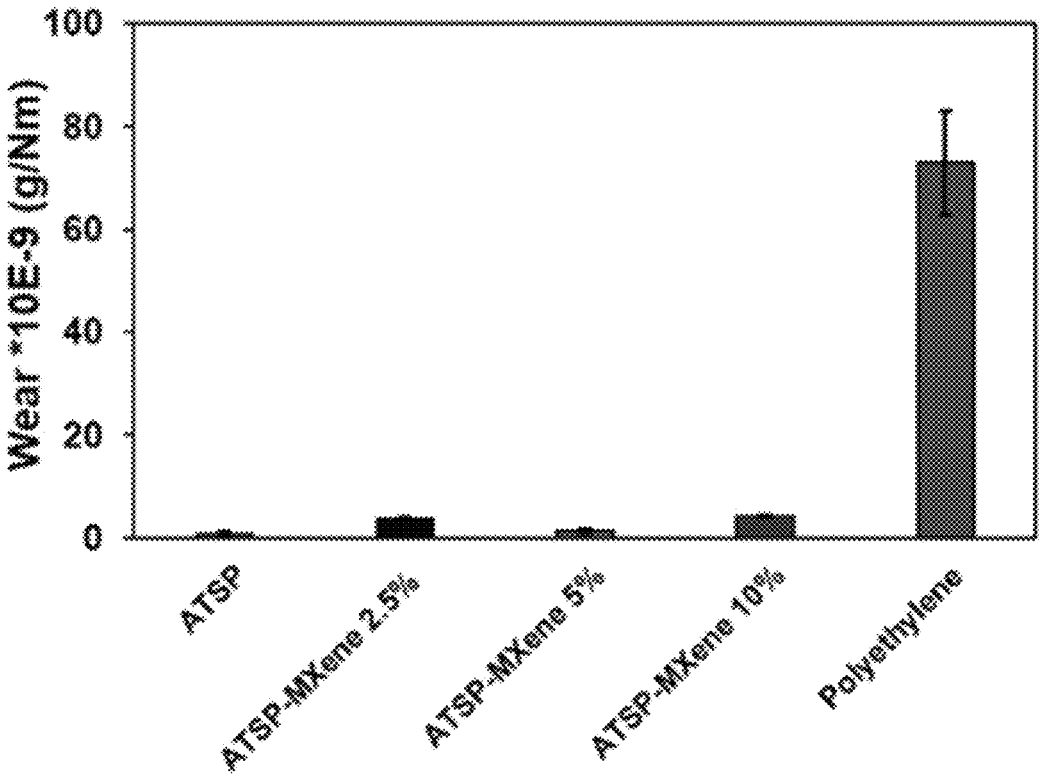
Figure 4D:
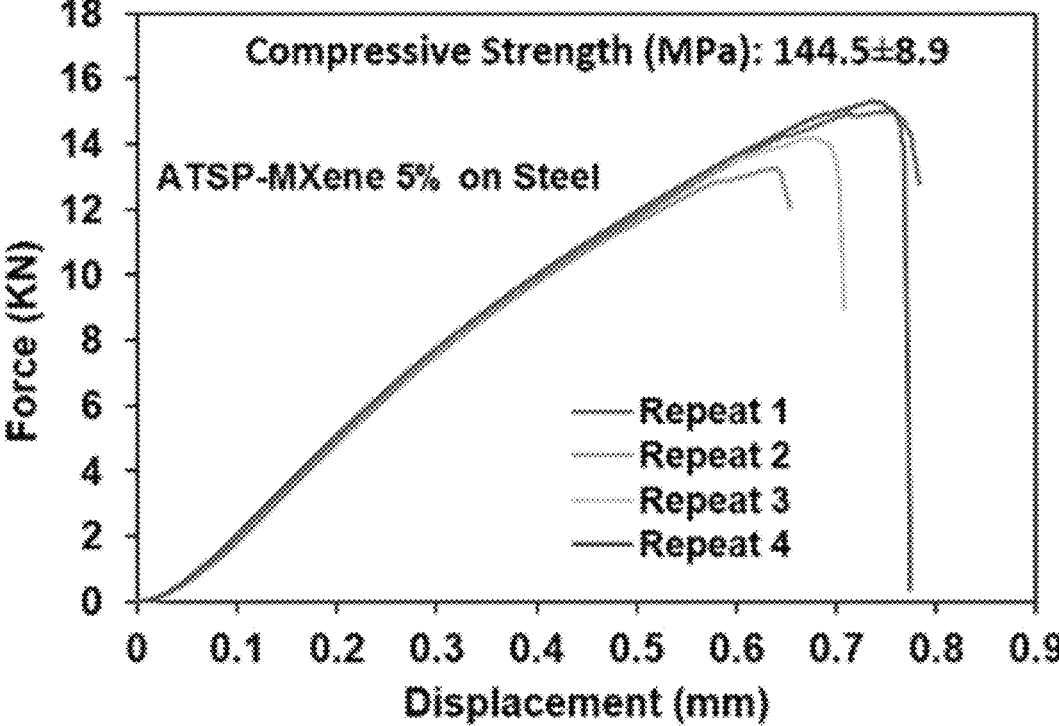
Figure 4E:
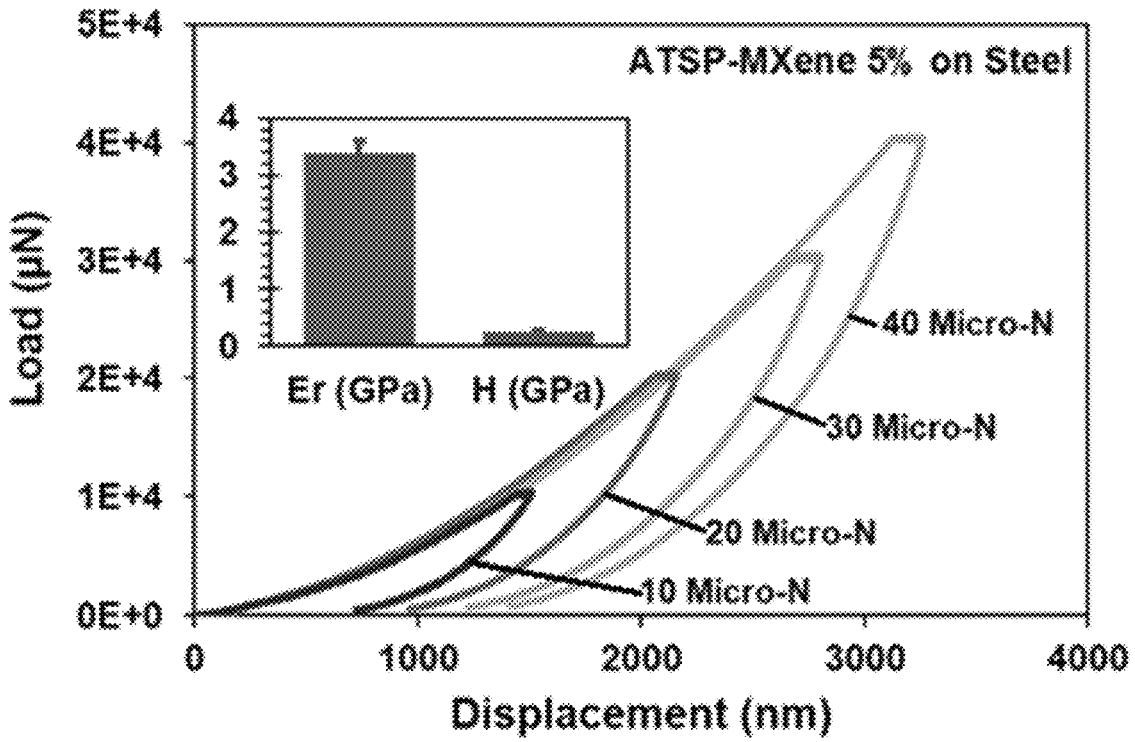
Figure 5A:
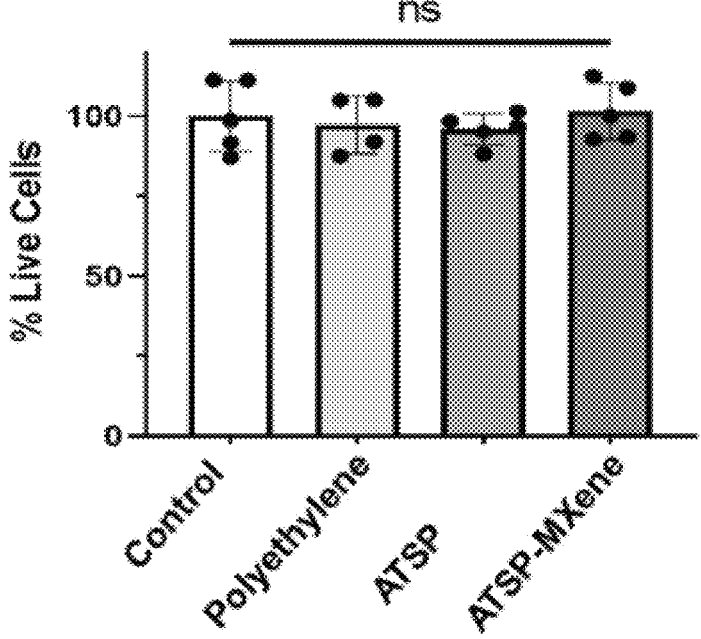
Figure 5B:
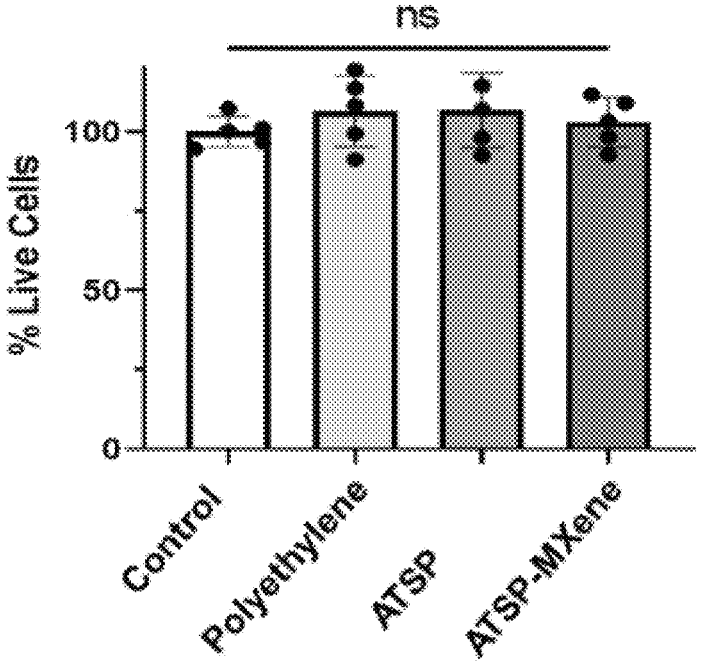
Figure 5C:
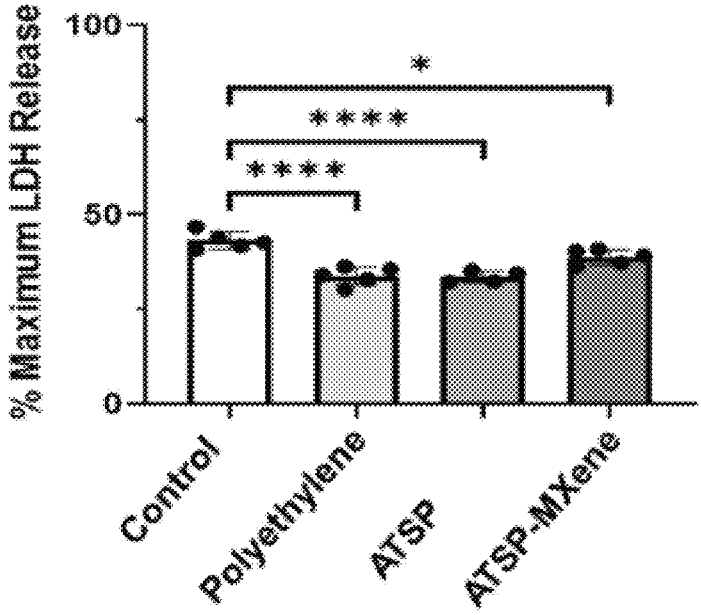
Figure 5D:
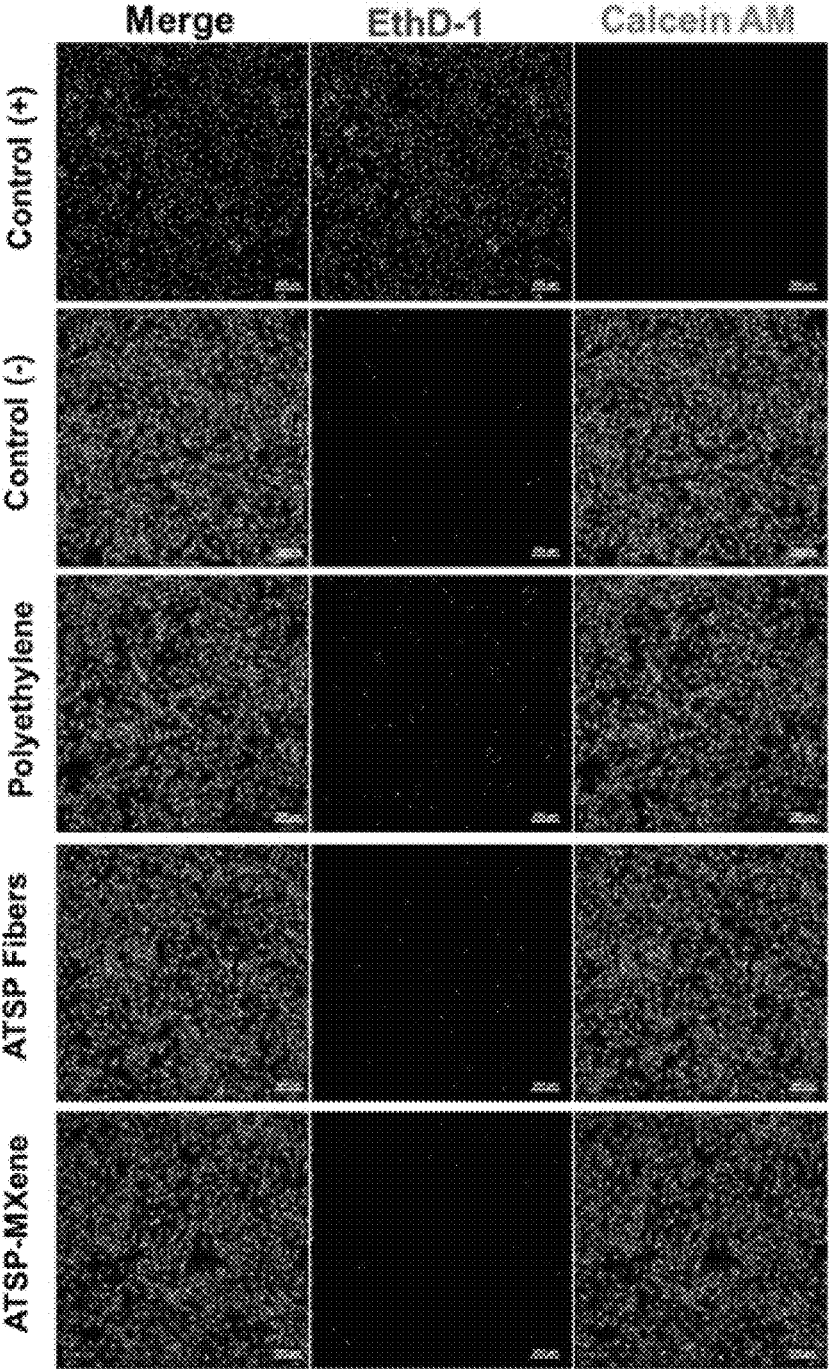
Figure 5E:
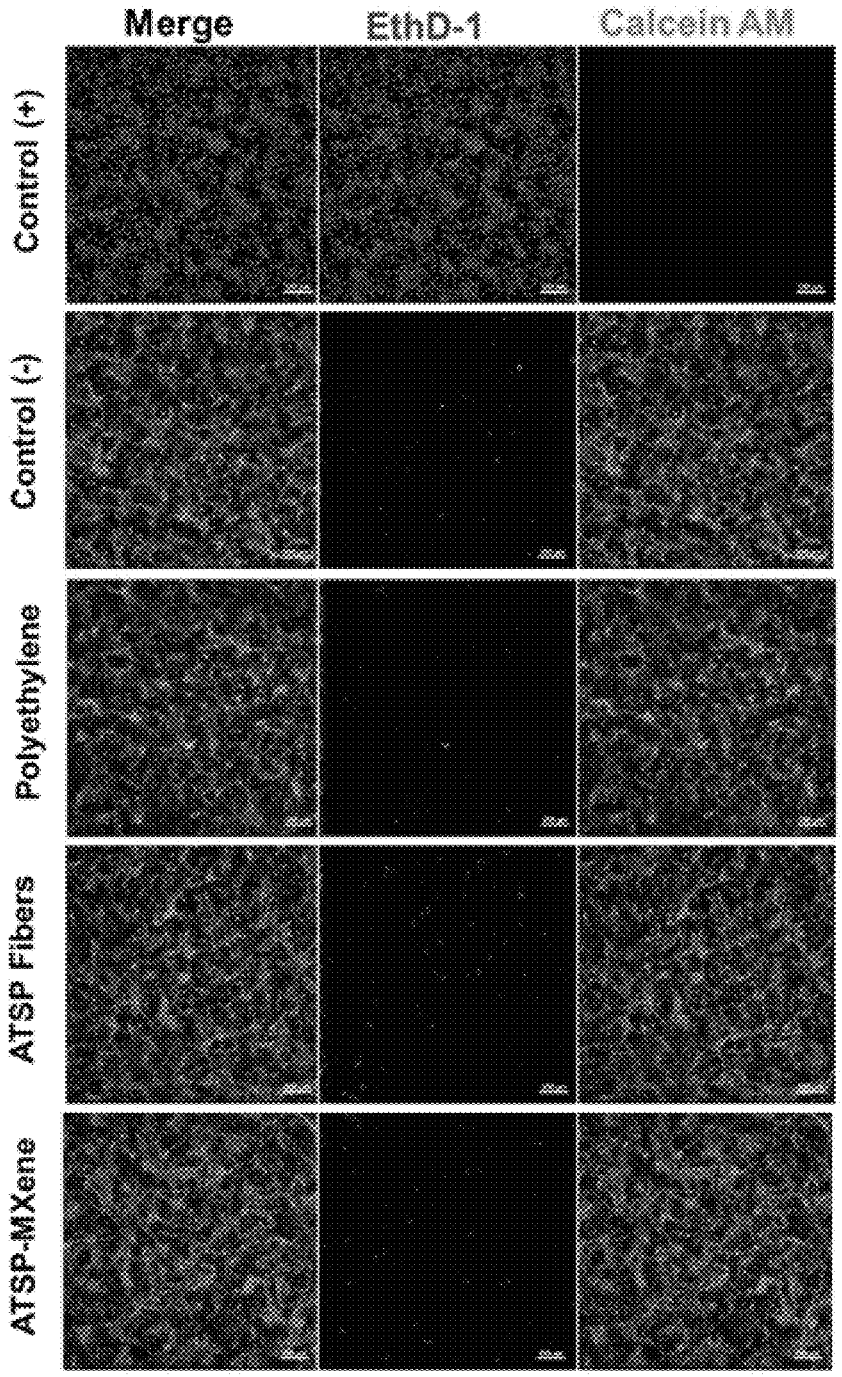

FIG. 4C compares the wear rate of neat ATSP, and ATSP-MXene nanocomposites at different concentrations with widely-used bio-grade polyethylene. As compared to polyethylene on polyethylene, both neat ATSP on neat ATSP and ATSP-MXene on ATSP-MXene samples presented almost "zero" wear rates, i.e., by nearly two orders of magnitude. Interestingly, both neat ATSP and 5 wt. % ATSP-MXene presented wear rate less than commonly-used bio-grade polyethylene/polyethylene and polyethylene/stainless steel joint implants. For example, while commonly-used polyethylene on stainless steel joint implants exhibited rate of $1.6 \times 10^{-9}$ g/Nm, the neat ATSP on neat ATSP and 5 wt. % ATSP-MXene on 5 wt. % ATSP-MXene samples exhibited lower wear rate of $0.85 \times 10^{-9}$ g/Nm and $1.3 \times 10^{-9}$ g/Nm, respectively, which are associated with 47% and 19% less wear rates. As evidenced above, 5 wt. % ATSP-MXene with a combination of dramatically low friction and low wear rate can be considered as a new generation of bioactive and stable material for implants. ATSP-based composites can be used to form a homogeneous tribofilm and fabricate mechanically strong biocompatible parts like hip and joints, as shown in FIGS. 4D-4E. It can also be a strong corrosion-resistant protection film for the steel surface. Additional to tribological experiments, other mechanical tests on 5 wt. % ATSP-MXene samples were performed, illustrating high compressive strength of 144.5 MPa (FIG. 4D), reduced modulus of 3.4 GPa and hardness of 0.26 GPa (FIG. 4E).

Therefore, since polymer-on-polymer hip joint bearings are at present under consideration as the next generation of alternatives to metal-on-metal and metal-on-polymer bearings, ATSP can be introduced as a promising material with outstanding mechanical and tribological properties. ATSP-MXene composites possess many factors such as high wear resistance, biocompatibility, mechanical integrity, and robustness as well as low friction. The ATSP-MXene composites are capable of undergoing compressive loads that are 2 orders of magnitudes greater than the body weight (the maximum predicted stresses in the medial region of 1.59 MPa). On the basis of the observed wear appearance, a polishing-type wear behavior was observed, resulting in extremely low wear rate.

Biocompatibility Evaluation

The biocompatibility of synthesized polyethylene, ATSP, and ATSP-MXene fibers was investigated when co-cultured with rat's bone marrow mesenchymal stem cells (MSC). Allogeneic MSCs are immunoprivilaged and their promising clinical applications for tissue engineering and regenerative medicine are under evaluation. Furthermore, MSCs possess high population doubling levels, telomere length, and have been previously characterized for their ability to differentiate into different cell types including osteogenic, adipogenic, and chondrogenic lineages. When experimental materials were co-cultured with these cell types for 24 h, assessment of biocompatibility using the LIVE/DEAD in-vitro test showed that all forms of the polyethylene, ATSP, and ATSP-MXene fibers were highly compatible with MSC and no significant change was observed compared to the control groups (almost 100% in all groups as shown in FIGS. 5A-5E). Additionally, the viability bioassay of the as-prepared fibers was evaluated on the effect of materials on cell survival, attachment, and proliferation after 120 h. The results showed that the fiber materials including polyethylene, ATSP, and ATSP-MXene are remarkably biocompatible with bone-marrow-derived MSCs and no significant change was observed in the cell morphology in vitro and physiological conditions, even on the 5th of the experiments. A similar trend and correlation between viability data of day-1 and day-5 conferred the accuracy of biocompatibility results.

Cells are well attached to the ATSP-based specimens without a significant undesired effect on the morphology and proliferation of the cells when compared to non-treated MSCs. Briefly, rat MSCs were co-cultured with specimens for 72 h. They were then fixed in 4% paraformaldehyde and stained with Alexa Fluor™ Plus 750 Phalloidin (A30105, Thermo Fisher Scientific). Specimens were then mounted onto microscope slides with ProLong™ Diamond Antifade Mountant with DAPI (P36971, Thermo Fisher Scientific). Images were captured on a Nikon Eclipse Ti2-E fluorescence microscope. Autofluorescence, GFP Filter; DAPI, DAPI Filter; Phalloidin, Cy7 Filter. The results show no significant change in the skeleton structure and morphology of the co-cultured cells compared to the control groups. Besides, the data demonstrate that significant numbers of mesenchymal stem cells (MSCs) are attached to the specimens, and their skeleton structure confirms the capability of the cultured specimens as a suitable substrate for promoting cell survival and growth (FIG. 13). Furthermore, the observed compatibility potentially supports further growth and targeted differentiation of MSCs for tissue engineering applications.

The LDH assessment is further examined to determine the toxicity effects of the materials. As it can be seen (FIGS. 5A-5E), no significant difference in maximum LDH release was detected between the experimental and control samples. The analysis confirmed excellent residual viability of cells and low differences within the experimental groups (n=5 per group). Remarkably, the significant decrease in LDH cytotoxicity of the fibers in comparison to control groups may also be beneficial in the development of cell proliferation and constructs. The results together confirmed that the as-prepared polyethylene, ATSP, and ATSP-MXene fibers are biocompatible with bone-marrow-derived MSC in-vitro ("ns"=statistically no significant difference, *=p<05 and =p<0.01, and **p s 0.0001). Taken together, these findings suggest that designed ATSP-MXene fibers can support the growth of osteogenic and chondrogenic mesenchymal stem cells for bone and joint repair.

Autofluorescence Properties

In the current study, the polyethylene, ATSP, and 5 wt. % ATSP-MXene fibers naturally displayed excellent autofluorescence properties at different excitation (377 nm-628 nm) and emission (447 nm-685 nm) wavelengths including blue, green, orange, and red fluorescent regions for targeted biomedical applications (FIG. 6). The dominant autofluorescence characterization of the synthesized fibers at different wavelengths was detected by the multi-mode Cytation5 imaging system. Furthermore, the interaction of cocultured fibers with bone-marrow MSCs has been qualitatively observed. In this regard, the auto-fluorescent fibers were detected by fluorescence microscopy with and without the presence of MSCs. As shown, all the samples displayed excellent fluorescence properties owing to the existence of such a variety of functional groups.

CONCLUSION

We introduced a novel composite (ATSP-MXene) for the first time as a promising material for the next generation of wear-free artificial bone implants. Outstanding biocompatibility of ATSP-MXene were confirmed by the growth of osteogenic and chondrogenic mesenchymal stem cells on them, making it a promising material for bone and joint repair either in coating form (due to excellent adhesive behavior during curing procedure) or bulk forms (due to excellent mechanical properties). ATSP-MXene composites at different concentrations were fabricated in both thin coating on a bio-grade steel and bulk forms and subsequently subjected to mechanical and biotribological tests. The results show the fabrication of an extremely-high wear-resistant composite, as compared to the widely-used bio-grade ultra-high molecular weight polyethylene. An enhanced implant material for bone and joint applications was identified at 5 wt % MXene. The hardness and modulus of the ATSP-MXene were extremely high, introducing it as an alternative for bulk applications as well. Possessing excellent tribological properties in the case of ATSP-MXene on ATSP-MXene joint pair, good adhesive properties, and appropriate mechanical properties are all the requirements to reduce the number of hip and knee replacements due to high wear rate and control aseptic loosening accompanied by periprosthetic osteolysis.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Altun, E. et al, The biocompatibility and characterization of aromatic thermosetting copolyester, University of Illinois at Urbana-Champaign Thesis (2018).
2. Amiri, A. et al, Porous nitrogen-doped MXene-based electrodes for capacitive deionization, Energy Storage Materials 25 (2020) 731-739.
3. Bakir, M. et al, Aromatic thermosetting copolyester nanocomposite foams: High thermal and mechanical performance lightweight structural materials, Polymer 123 (2017) 311-320.
4. Bashandeh, K. et al, Extreme environment tribological study of advanced bearing polymers for space applications, Tribology International 153 (2021) 106634.
5. Bashandeh, K. et al, Tribological performance of graphene and PTFE solid lubricants for polymer coatings at elevated temperatures, Tribology Letters 67 (2019) 1-14.
6. Beadling, A. et al, A link between the tribology and corrosive degradation of metal-on-metal THRs, Tribology International 113 (2017) 354-361.
7. Brockett, C. L. et al, PEEK and CFR-PEEK as alternative bearing materials to UHMWPE in a fixed bearing total knee replacement: An experimental wear study, Wear 374-375 (2017) 86-91.
8. Economy, J. et al, Polymer coating system for improved tribological performance, Google Patents, 2017.
9. Eom, W. et al, Large-scale wet-spinning of highly electroconductive MXene fibers, Nature communications 11 (2020) 1-7.
10. Felson, D. T. et al, The prevalence of knee osteoarthritis in the elderly. The Framingham Osteoarthritis Study, Arthritis & Rheumatism: Official Journal of the American College of Rheumatology 30 (1987) 914-918.

11. Halim, J. et al, Transparent conductive two-dimensional titanium carbide epitaxial thin films, Chemistry of Materials 26 (2014) 2374-2381.

12. Han, Y. et al, Biomimetic injectable hydrogel microspheres with enhanced lubrication and controllable drug release for the treatment of osteoarthritis, Bioactive materials 6 (2021) 3596-3607.

13. Huang, K. et al, Two-dimensional transition metal carbides and nitrides (MXenes) for biomedical applications, Chemical Society Reviews 47 (2018) 5109-5124.

14. Jacobs, J. J. et al, Osteolysis: basic science, Clinical Orthopaedics and Related Research® 393 (2001) 71-77.

15. Jordan, J. M. et al, Prevalence of knee symptoms and radiographic and symptomatic knee osteoarthritis in African Americans and Caucasians: the Johnston County Osteoarthritis Project, The Journal of rheumatology 34 (2007) 172-180.

16. Kaivosoja, E. et al, Materials used for hip and knee implants, Wear of orthopaedic implants and artificial joints, Woodhead Publishing Limited 2012.

17. Katz, J. N. et al, Diagnosis and treatment of hip and knee osteoarthritis: a review, Jama 325 (2021) 568-578.

18. Kurtz, S. M. et al, Impact of the economic downturn on total joint replacement demand in the United States: updated projections to 2021, JBJS 96 (2014) 624-630.

19. Kurtz, S. M. et al, PEEK biomaterials in trauma, orthopedic, and spinal implants, Biomaterials 28 (2007) 4845-4869.

20. Kwon, Y.-M. et al, Risk stratification algorithm for management of patients with metal-on-metal hip arthroplasty: consensus statement of the American Association of Hip and Knee Surgeons, the American Academy of Orthopaedic Surgeons, and the Hip Society, JBJS 96 (2014) e4.

21. Lan, P. et al, Tribological performance of aromatic thermosetting polyester (ATSP) coatings under cryogenic conditions, Wear 398 (2018) 47-55.

22. Lan, P. et al, Unlubricated tribological performance of aromatic thermosetting polyester (ATSP) coatings under different temperature conditions, Tribology Letters 61 (2016) 10.

23. Lausmaa, J. et al, Surface spectroscopic characterization of titanium implant materials, Applied Surface Science 44 (1990) 133-146.

24. Lin, X. et al, Injectable Natural Polymer Hydrogels for Treatment of Knee Osteoarthritis, Advanced Healthcare Materials (2021) 2101479.

25. Liu, G. et al, Tuning the tribofilm nanostructures of polymer-on-metal joint replacements for simultaneously enhancing anti-wear performance and corrosion resistance, Acta biomaterialia 87 (2019) 285-295.

26. Lodge, F. et al, Prevalence of subclinical cardiac abnormalities in patients with metal-on-metal hip replacements, International journal of cardiology 271 (2018) 274-280.

27. Losina, E. et al, Lifetime risk and age at diagnosis of symptomatic knee osteoarthritis in the US, Arthritis care & research 65 (2013) 703-711.

28. Mai, K I et al, Incidence of 'squeaking' after ceramic-on-ceramic total hip arthroplasty, Clinical Orthopaedics and Related Research 468 (2010) 413-417.

29. Marian, M. et al, Effective usage of 2D MXene nanosheets as solid lubricant-Influence of contact pressure and relative humidity, Applied Surface Science 531 (2020) 147311.

30. Martin, T. R. et al, An evaluation of the toxicity of carbon fiber composites for lung cells in vitro and in vivo, Environmental Research 49 (1989) 246-261.

31. Mencer Jr, D. et al, Surface reactivity of titanium-aluminum alloys: $Ti3Al$, $TiAl$, and $TiAl3$, Journal of Vacuum Science & Technology A: Vacuum, Surfaces, and Films 9 (1991) 1610-1615.

32. Naguib, M. et al, Ten years of progress in the synthesis and development of MXenes, Advanced Materials 33 (2021) 2103393.

33. Ormsby, R. T. et al, Evidence that osteocyte perilacunar remodelling contributes to polyethylene wear particle induced osteolysis, Acta biomaterialia 33 (2016) 242-251.

34. Patel, A. K. et al, Carbon nanotube functionalization decreases osteogenic differentiation in aluminum oxide reinforced ultrahigh molecular weight polyethylene, ACS Biomaterials Science & Engineering 2 (2016) 1242-1256.

35. Pourzal, R. et al, How does wear rate compare in well-functioning total hip and knee replacements? A postmortem polyethylene liner study, Clinical Orthopaedics and Related Research® 474 (2016) 1867-1875.

36. Rafieerad, A. et al, Application of $Ti3C2$ MXene quantum dots for immunomodulation and regenerative medicine, Advanced healthcare materials 8 (2019) 1900569.

37. Rafieerad, A. et al, Fabrication of Smart Tantalum Carbide MXene Quantum Dots with Intrinsic Immunomodulatory Properties for Treatment of Allograft Vasculopathy, Advanced Functional Materials (2021) 2106786.

38. Rafieerad, A. et al, Sweet-MXene hydrogel with mixed-dimensional components for biomedical applications, Journal of the mechanical behavior of biomedical materials 101 (2020) 103440.

39. Rakow, A. et al, Influence of particulate and dissociated metal-on-metal hip endoprosthesis wear on mesenchymal stromal cells in vivo and in vitro, Biomaterials 98 (2016) 31-40.

40. Rao, A. J. et al, Revision joint replacement, wear particles, and macrophage polarization, Acta biomaterialia 8 (2012) 2815-2823.

41. Regis, M. et al, Wear behavior of medical grade PEEK and CFR PEEK under dry and bovine serum conditions, Wear 408 (2018) 86-95.

42. Sareen, N. et al, Early passaging of mesenchymal stem cells does not instigate significant modifications in their immunological behavior, Stem cell research & therapy 9 (2018) 1-11.

43. Seo, B.-B. et al, Injectable polymeric nanoparticle hydrogel system for long-term anti-inflammatory effect to treat osteoarthritis, Bioactive Materials 7 (2022) 14-25.

44. Soleymaniha, M. et al, Promoting role of MXene nanosheets in biomedical sciences: therapeutic and biosensing innovations, Advanced healthcare materials 8 (2019) 1801137.

45. Song, J. et al, Fretting wear study of PEEK-based composites for bio-implant application, Tribology Letters 65 (2017) 1-11.

46. Song, J. et al, In vitro wear study of PEEK and CFRPEEK against UHMWPE for artificial cervical disc application, Tribology International 122 (2018) 218-227.

47. Sykaras, N. et al, Implant materials, designs, and surface topographies: their effect on osseointegration. A literature review, International Journal of Oral & Maxillofacial Implants 15 (2000).

48. Tetreault, M. W. et al, Adverse local tissue reaction after a metal-on-metal total hip prosthesis without elevated serum metal ion levels, Orthopedics 41 (2018) e438-e441.

49. Thienkarochanakul, K. et al, Stress Distribution of the Tibiofemoral Joint in a Healthy Versus Osteoarthritis Knee Model Using Image-Based Three-Dimensional Finite Element Analysis, Journal of Medical and Biological Engineering 40 (2020) 409-418.

50. Utzschneider, S. et al, Inflammatory response against different carbon fiber-reinforced PEEK wear particles compared with UHMWPE in vivo, Acta biomaterialia 6 (2010) 4296-4304.

51. Vos, T. et al, Global, regional, and national incidence, prevalence, and years lived with disability for 301 acute and chronic diseases and injuries in 188 countries, 1990-2013: a systematic analysis for the Global Burden of Disease Study 2013, The lancet 386 (2015) 743-800.

52. Wyatt, H. et al, The effect of engineered surface topography on the tribology of CFR-PEEK for novel hip implant materials, Biotribology 7 (2016) 22-30.

53. Zeman, J. et al, UHMWPE acetabular cup creep deformation during the run-in phase of THA's life cycle, Journal of the mechanical behavior of biomedical materials 87 (2018) 30-39.

54. Zhang, J. et al, A new family of low wear, low coefficient of friction polymer blend based on polytetrafluoroethylene and an aromatic thermosetting polyester, Polymers for Advanced Technologies 19 (2008) 1105-1112.

55. Zhang, S. et al, In vitro and in vivo biocompatibility and osteogenesis of graphene-reinforced nanohydroxyapatite polyamide66 ternary biocomposite as orthopedic implant material, International journal of nanomedicine 11 (2016) 3179.

56. Zhang, X. et al, Implanted 3D gelatin microcryogel enables low-dose cell therapy for osteoarthritis by preserving the viability and function of umbilical cord MSCs, Chemical Engineering Journal 416 (2021) 129140.

57. Zhou, T. et al, Super-tough MXene-functionalized graphene sheets, Nature communications 11 (2020) 1-11.

What is claimed is:

1. A medical implant comprising a composite material, wherein the composite material comprises an aromatic thermosetting copolyester (ATSP) and an MXene.

2. The medical implant of claim 1, wherein the MXene is present at from about 0.1 wt % to about 10 wt % relative to the aromatic thermosetting copolyester.

3. The medical implant of claim 1, wherein the medical implant comprises a screw, a pin, a plate, a mesh, a valve, a fiber, an artificial joint, a dental implant, or a stabilizing device.

4. The medical implant of claim 1, wherein the composite material is present as a coating on a second material.

5. The medical implant of claim 4, wherein the coating has a thickness of from about 10 to about 120 μm.

6. The medical implant of claim 4, wherein the second material comprises stainless steel, a ceramic, titanium or a titanium alloy, polyethylene, neat ATSP, polyether ether ketone (PEEK), a cobalt-chromium alloy, another medical grade implant material, or any combination thereof.

7. The medical implant of claim 1, wherein at least two contacting surfaces of the medical implant comprise the composite material.

8. The medical implant of claim 1, wherein the composite material comprises a three dimensional structure.

9. The medical implant of claim 1, wherein the aromatic thermosetting copolyester comprises a random copolymer comprising crosslinked oligomers, wherein the oligomers comprise two or more monomers.

10. The medical implant of claim 9, wherein the two or more monomers comprise trimesic acid (TMA), 4-acetoxybenzoic acid (ABA), isophthalic acid (IPA), biphenol diacetate (BPDA), or any combination thereof.

11. The medical implant of claim 9, wherein the oligomers have molecular weights of from about 400 to about 2000 kDa.

12. The medical implant of claim 1, further comprising an additive.

13. The medical implant of claim 12, wherein the additive comprises $MoS_2$, graphene, polytetrafluoroethylene (PTFE), or any combination thereof.

14. The medical implant of claim 1, wherein the MXene has the formula $Ti_3C_2T_x$, wherein $T_x$ comprises one or more terminal groups selected from —OH, —COOH, —O, —F, or any combination thereof.

15. The medical implant of claim 1, wherein the medical implant is biocompatible.

16. The medical implant of claim 1, wherein the medical implant, the coating if present, or both are wear-resistant.

17. A method for making a composite material comprising an aromatic thermosetting copolyester and an MXene, the method comprising:

(a) curing a mixture of one or more ATSP precursor powders and one or more MXenes to produce a first cured material;

(b) grinding the first cured material to form a second powder;

(c) curing the second powder to form a second cured material; and (d) grinding the second cured material to form a final powder form.

18. The method of claim 17, further comprising molding the final powder form into a solid bulk composite.

19. The method of claim 18, wherein molding is conducted under a pressure of from about 10 MPa to about 41 MPa and is carried out at a temperature of from about 340° C. to about 360° C.

20. The method of claim 17, wherein the one or more ATSP precursor powders comprise a monomer having carboxylic acid terminal groups, a monomer having acetoxy terminal groups, or any combination thereof.

* * * * *